US007052697B1

(12) United States Patent
Hasse et al.

(10) Patent No.: US 7,052,697 B1
(45) Date of Patent: May 30, 2006

(54) *LAWSONIA* DERIVED GENE AND RELATED OMPH POLYPEPTIDES, PEPTIDES AND PROTEINS AND THEIR USES

(75) Inventors: Detlef Hasse, Sunbury (AU); Michael Panaccio, North Balwyn (AU); Meri Sinistaj, East St. Kilda (AU)

(73) Assignees: Agriculture Victoria Services PTY LTD, Victoria (AU); Pig Research and Development Corp., Australian Capital Territory (AU)

( * ) Notice: Subject to any disclaimer, the term of this patent is extended or adjusted under 35 U.S.C. 154(b) by 0 days.

(21) Appl. No.: 10/018,290

(22) PCT Filed: May 11, 2000

(86) PCT No.: PCT/AU00/00438

§ 371 (c)(1),
(2), (4) Date: Apr. 16, 2002

(87) PCT Pub. No.: WO00/69905

PCT Pub. Date: Nov. 23, 2000

Related U.S. Application Data

(60) Provisional application No. 60/133,986, filed on May 13, 1999.

(51) Int. Cl.
*A61K 39/02* (2006.01)
*A61K 39/00* (2006.01)
*C07K 14/195* (2006.01)

(52) U.S. Cl. .............................. 424/190.1; 424/234.1; 424/184.1; 530/350

(58) Field of Classification Search .............. 424/93.4, 424/184.1, 190.1, 234.1; 435/69.1, 69.3, 435/243, 252.1, 252.3, 320.1; 514/2; 530/300, 530/350, 403
See application file for complete search history.

(56) References Cited

U.S. PATENT DOCUMENTS 5,885,823 A * 3/1999 Knittel et al. ............... 435/243

FOREIGN PATENT DOCUMENTS

| AU | WO 97/20050 | * 6/1997 |
|---|---|---|
| WO | PCT WO 96/39629 | 12/1996 |
| WO | PCT WO 97/20040 | 6/1997 |

OTHER PUBLICATIONS

McCluskey et al., Infection and Immunity, vol. 70 No 6, pp. 2899-2907 (Jun. 2002).*
Bowie et al., Science, Vlume 247 No 4948 (Mar. 1990).*
Riffkin et al., Gene, colume 167, pp. 279-283 (1995).*
Pinnila et al., Molecular Immunology, Colume 30 No 6, pp. 577-585 (1993).*
Guedes et al., Veterinary Microbiology, vol. 91 No 2-3, pp. 135-145 (Feb. 2003).*
Guedes et al., Veterinary Microbiology, vol. 93 No 2, pp. 159-166 (May 2003).*
Kroll et al., American Journal of Veterinary Research, vol. 65, No 5, pp. 559-565 (May 2004).*
Basaraba, R.J., Byerly, A.N. Stewart, G.C., Mosier, D.A. Fenwick, B.W., Chengappa, M.M., and Laegreid, W.W., "Actin enhances the haemolytic activity of *Escherichia coli*," *Microbiology*, 144:1845-1852 (1998).
Nollau, P., Moser, C. Wagener, *BioTechniques*, 20:784-788 (1996).
Boye et al., Specific Detection of *Lawsonia intracellularis* in Porcine Proliferation Enteropathy Inferred From Fluorecent rRNA In Situ Hybridization, Vet Pathol 35:153-156 (1998).
Altuvia, Y. et al., *J. Mol. Biol.*, 249:244-250 (1995).
Amann and Brosius, *Gene*, 40:183 (1985).
Anderson, B.J. et al., *Journal of Bacteriology*, 160:748-754 (1984).
Barker, I.K. et al., "Pathology of Domestic Animals," 3rd Edition, vol. 2, 1-37, eds., K.V.F. Jubb, P.C. Kennedy, and N. Palmer (Academic Press: Orlando) (1985).
DeGroot, A.S. et al., *Vaccines*, 96, Cold Spring Harbor Laboratory, Cold Spring Harbor, NY (1995).
Devereux, J. et al., *Nucl. Acids Res.*, 12:387-395 (1984).
Elwell, M.R. et al., *Veterinary Pathology*, 18:136-139 (1981).
Fox, J.G. et al., *Veterinary Pathology*, 26:515-517 (1989).
Gebhart, C.J. et al., *American Journal of Veterinary Research*. 44:361-367 (1983).
Gish, W. et al., *Nature Genetics*, 3:266-272 (1993).
Goodman et al., *Biopolymers*, 26:525-532 (1987).
Huse et al, *Science*, 246:1275-1281 (1989).
Jones et al, *Am. J. Vet. Res.*, 58:1125-1131 (1997).
Jonsson, L. et al, *Acta Veterinaria Scandinavica*, 17:223-232 (1976).

(Continued)

*Primary Examiner*—James Housel
*Assistant Examiner*—Zachariah Lucas
(74) *Attorney, Agent, or Firm*—Thomas A. Wootton; Kohn & Associates, PLLC; Kenneth I. Kohn

(57) ABSTRACT

The present invention relates generally to therapeutic compositions for the treatment and/or prophylaxis of intestinal disease conditions in animals and birds caused or exacerbated by *Lawsonia intracellularis* or similar or otherwise related microorganism. In particular, the present invention provides a novel gene derived from *Lawsonia intracellularis* which encodes an immunogenic OmpH peptide, polypeptide or protein that is particularly useful as an antigen in vaccine preparation for conferring humoral immunity against *Lawsonia intracellularis* and related pathogens in animal hosts. The present invention is also directed to methods for the treatment and/or prophylaxis of such intestinal disease conditions and to diagnostic agents and procedures for detecting *Lawsonia intracellularis* or similar or otherwise related microorganisms.

4 Claims, 10 Drawing Sheets

OTHER PUBLICATIONS

Kohler and Milstein, *Nature*, 256:495-499 (1975).
Kozbor et al., *Immunol. Today*. 4:72 (1983).
Lawson et al., *Journal of Clinical Microbiology*, 31:1136-1142 (1993).
Love, R.J. et al., *Veterinary Record*, 100:473 (1977).
Margalit, H. et al., *J. Immunol.*, 138:2213-2229 (1987).
Mason, R.W. et al., *Australian Veterinary Journal* (1998).
McOrist, S., et al., *The Veterinary Record*, 121:421-422 (1987).
McOrist, S. et al., *Infection and Immunity*, 61:4286-4292 (1993).
McOrist, S. et al., *International Journal of Systematic Bacteriology*, 45:820-925 (1995).
Meister et al., *Vaccine*, 13:581-591 (1995).
Mierke et al., *Int. J. Peptide Protein Research*, 35:35-45 (1990).
Mohapatra, S.S. et al., *Allergy*, 50:37-44 (1995).
Needleman and Wunsch, *J. Mol. Biol.*, 48:443-453 (1970).
O'Neil, I., P.A. *Veterinary Record*, 87:742-747 (1970).
Parker, K.C. et al., *J. Immunol.*, 152:163-175 (1994).
Portoghese et al., *J. Med. Chem.*, 33:1714-1720 (1990).
Reinhartz, A. et al., *Gene*, 136:221-226 (1993).
Rowland, A.C. et al. *Veterinary Record*, 97:178-180 (1976).
Schodeb, T.R. et al., *Veterinary Pathology*, 27:73-80 (1990).
Shimatake and Rosenberg, *Nature*, 292:128 (1981).
Stills, H.F., *Infection and immunology*, 59:3227-3236 (1991).
Straw, B.E., *Journal of American Veterinary Medical Association*, 197:355-357 (1990).
Studier and Moffat, *J. Mol. Biol.*, 189:113 (1986).
Thompson, J.D. et al., *Nucl. Acids Res.*, 22:4673-4680 (1994).
Vajda, S. et al., *Biopolymers*, 29:1755-1772 (1990).
Van Regenmortel, "Molecular dissection of protein antigens," *Structure of antigens*, 1-27 (1992).

* cited by examiner

| 3(iii) | 3(vi) |
|---|---|
| 3(ii) | 3(v) |
| 3(i) | 3(iv) | 3(vii) |

```
L. int    - - - - - - - - - - - - M K V K    Q S I A M E S E A A K A V Q
Y. pseud  - - - - - - - - - - - - - - - -    - S H Q Q L P R A D R E A V A
Y. enter  - - - - - - - - - - - - M K - K    - S I Q Q H P A R R E T V A
H. influ  - - - - - - - - - - - - M E N -    - G Y I R E K A D R I Q A A Q
A. aeoli  - - - - - - - - - - - - M K - K    - N K S Q V A F I K A K G V
E. coli   - - - - - - - - - - - - M K - K    - G S L Q Q L P D R K G G V S
S. typhi  - - - - - - - - - - - - M K - K    - G N F Q E L A Q L A K E S
C. trach  M A K N N T R H Y S L R R K L F    - R R C L R E R H N K D R A R
S. pyoge  - - - - - - - - - - - - - L - K    I Q N I Y H F H P - D P A V A
9701638   - - - - - - - - - - - - M K N I    H G   I                     
```

Figure 3(ii)

Figure 3(iii)

|            | P | E | M | A | N | R | K | K |
|------------|---|---|---|---|---|---|---|---|
| L. int     | – | – | – | – | – | – | – | – |
| Y. pseud   | – | – | – | – | – | – | – | – |
| Y. enter   | – | – | – | – | – | – | – | – |
| H. influ   | – | – | – | – | – | – | – | – |
| A. aeoli   | – | – | – | – | – | – | – | – |
| E. coli    | – | – | – | – | – | – | – | – |
| S. typhi   | – | – | – | – | – | – | – | – |
| C. trach   | – | – | – | – | – | – | – | – |
| S. pyoge   | I | R | – | – | – | – | – | – |
| 9701638

US 7,052,697 B1

LAWSONIA DERIVED GENE AND RELATED OMPH POLYPEPTIDES, PEPTIDES AND PROTEINS AND THEIR USES

This is the U.S. National phase under 35 U.S.C. §371 of International application PCT/AU00/00438, filed May 11, 2000, and claims priority to U.S. Provisional Application 60/133,986, filed May 13, 1999, both of which are herein incorporated by reference.

FIELD OF THE INVENTION

The present invention relates generally to therapeutic compositions for the treatment and/or prophylaxis of intestinal disease conditions in animals and birds caused or exacerbated by *Lawsonia intracellularis* or similar or otherwise related microorganism. In particular, the present invention provides a novel gene derived from *Lawsonia intracellularis* which encodes an immunogenic peptide, polypeptide or protein. The polypeptide described herein, designated as OmpH, or a peptide homologue, analogue or derivative thereof is particularly useful as an antigen in vaccine preparation for conferring humoral immunity against *Lawsonia intracellularis* and related pathogens in animal hosts. The present invention is also directed to methods for the treatment and/or prophylaxis of such intestinal disease conditions and to diagnostic agents and procedures for detecting *Lawsonia intracellularis* or similar or otherwise related microorganisms.

GENERAL

Bibliographic details of the publications numerically referred to in this specification are collected at the end of the description. All patents, patent applications, and publications cited herein are incorporated by reference in their entirety.

Reference hereinafter to "*Lawsonia intracellularis*" or its abbreviation "*L. intracellularis*" includes all microorganisms similar to or otherwise related to this microorganism, as described by Stills (1991) or Jones et al.(1997) or Lawson et al. (1993) or McOrist et al. (1995).

As used herein, the word "ompH", or the term "ompH gene", shall be taken to refer to the gene encoding the OmpH polypeptide of the present invention.

As used herein the term "derived from" shall be taken to indicate that a specified product, in particular a macromolecule such as a peptide, polypeptide, protein, gene or nucleic acid molecule, antibody molecule, Ig fraction, or other macromolecule, or a biological sample comprising said macromolecule, may be obtained from a particular source, organism, tissue, organ or cell, albeit not necessarily directly from that source, organism, tissue, organ or cell.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps, features, compositions and compounds.

The present invention is not to be limited in scope by the specific embodiments described herein, which are intended for the purposes of exemplification only. Functionally equivalent products, compositions and methods are clearly within the scope of the invention, as described herein.

BACKGROUND OF THE INVENTION

The meat-producing sector of the agricultural industry is dependent upon the health of its livestock and there is a need to maintain disease-free livestock for human consumption. The industry is subject to rapid economic downturn in response to disease conditions adversely affecting livestock and the quality of meat products derived therefrom, including those diseases which may potentially be transmitted to humans. It is important, therefore, to have well defined treatments and prophylactic and diagnostic procedures available to deal with infections or potential infections in livestock animals and humans.

Meat products derived from porcine and avian species are significant commercial products in the agriculture industry. In particular, pigs form a major component of the meat industry. However, pigs are sensitive to a wide spectrum of intestinal diseases collectively referred to as porcine proliferative enteropathy (PPE). These diseases have previously been known as intestinal adenomatosis complex (Barker and van Drumel, 1985), porcine intestinal adenomatosis (PIA), necrotic enteritis (Rowland and Lawson, 1976), proliferative haemorrhagic enteropathy (Love and Love, 1977), regional ileitis (Jonsson and Martinsson, 1976), haemorrhagic bowel syndrome (O'Neil, 1970), porcine proliferative enteritis and *Campylobacter* spp—induced enteritis (Straw, 1990).

There are two main forms of PPE: a non-haemorrhagic form represented by intestinal adenomatosis which frequently causes growth retardation and mild diarrhoea; and a haemorrhagic form, which is often fatal, represented by proliferative haemorrhagic enteropathy (PHE), where the distal small intestine lumen becomes engorged with blood. PPE has been reported in a number of animal species including pigs (McOrist et al, 1993), hamsters (Stills, 1991), ferrets (Fox et al, 1989), guinea pigs (Elwell et al, 1981), rabbits (Schodeb and Fox, 1990) as well as avian species (Mason et al, 1998).

The causative organism of PPE is a *Campylobacter*-like organism referred to herein as "*Lawsonia intracellularis*" (McOrist et al, 1995). The organism has also been previously referred to as *Ileal symbiont intracellularis* (Stills, 1991). PPE like diseases in pigs may also be caused by other pathogens such as various species of *Campylobacter* (Gebhart et al, 1983).

*Lawsonia intracellularis* is an intracellular, possibly obligate intracellular, bacterium. It can only be cultured in vitro with tissue culture cells (Jones et al., 1997; Lawson et al., 1993; McOrist et al, 1995; International Patent Application No. PCT/US96/09576). *L. intracellularis* is located in the cytoplasm of the villus cells and intestinal crypt cells of infected animals. Pigs suffering from PPE are characterised by irregularities in the villus cells and intestinal crypt structure with epithelial cell dysplasia, wherein crypt abscesses form as the villi and intestinal crypts become branched and fill with inflammatory cells.

PPE is a significant cost component associated with the pig industry, especially in terms of stock losses, medication costs, reduced growth rates of pigs and increased feed costs. PPE also contributes to downstream indirect costs in, for example, additional labour costs and environmental costs in dealing with antibiotic residue contamination, and in control measures to prevent the organism from being passed on or carried to other animals or humans.

Current control strategies for PPE rely on the use of antibacterials. However, such a strategy is considered to only be short to medium term, especially since governmental regulatory pressures tend to discourage animal husbandry practices which involve the use of prophylactic antibiotics. There is a need, therefore, to develop effective, safe and low cost alternatives to the use of antibiotics and, in particular, to develop vaccine preparations capable of conferring protective immunity against Lawsonia intracellularis infection in livestock animals.

The most effective vaccine preparations are generally comprised of a highly antigenic component, such as a peptide, polypeptide, protein or other macromolecule which is derived from the pathogenic organism against which the vaccine is directed, wherein said antigenic component produces little or no contraindications when administered to a susceptible host animal, and produces little or no antigenic cross-reactivity with desirable organisms, such as non-pathogenic organisms that are a part of the normal flora of the intestinal tract or other tissues of said host animal. In summary, an effective vaccine preparation must be immunogenic, specific and safe.

Accordingly, there is a need to identify highly immunogenic antigens produced by the bacterium Lawsonia intracellularis.

International Patent Application No. PCT/AU96/00767 describes several L. intracellularis partial genetic sequences, and partial polypeptides encoded thereby. However, there is a need to further identify polypeptide immunogens produced by the bacterium L. intracellularis and immunogenic peptides derived therefrom, including those immunogens which are genus- or species-specific, for use in improved vaccine compositions. The presently-described invention provides such immunogens.

SUMMARY OF THE INVENTION

One aspect of the present invention is directed to an isolated or recombinant immunogenic polypeptide which comprises, mimics or cross-reacts with a B-cell or T-cell epitope of the OmpH polypeptide derived from Lawsonia spp. Preferably, the isolated or recombinant immunogenic polypeptide is selected from the group consisting of the following:
  (i) a peptide, oligopeptide or polypeptide which comprises an amino acid sequence which has at least about 60% sequence identity overall to the amino acid sequence set forth in SEQ ID NO: 1;
  (ii) a peptide, oligopeptide or polypeptide which comprises at least about contiguous amino acids of the amino acid sequence defined by SEQ ID NO: 1; or
  (iii) a homologue, analogue or derivative of (i) or (ii), which mimics a B-cell or T-cell epitope of Lawsonia spp.

In a preferred embodiment, the polypeptide comprises or consists essentially of the amino acid sequence of SEQ ID NO:1.

A further aspect of the present invention provides a vaccine composition for the prophylaxis or treatment of infection in an animal, such as a pig or bird, by L. intracellularis or a similar or otherwise related microorganism, said vaccine composition comprising an immunologically effective amount of an immunogenic component which comprises an isolated or recombinant polypeptide having at least about 60% overall sequence identity to the amino acid sequence set forth in SEQ ID NO: 1 or comprising at least 5 contiguous amino acids derived from SEQ ID NO: 1 or an immunogenic homologue, analogue or derivative thereof which is immunologically cross-reactive with Lawsonia intracellularis; and one or more carriers, diluents and/or adjuvants suitable for veterinary or pharmaceutical use.

In a preferred embodiment, the polypeptide of the vaccine composition comprises or consists essentially of the amino acid sequence of SEQ ID NO: 1.

A further aspect of the invention extends to an immunologically interactive molecule, such as an antibody or antibody fragment, which is capable of binding to the immunogenic polypeptide of the invention.

A further aspect of the invention provides a method of diagnosing infection of an animal by Lawsonia intracellularis or a related microorganism, said method comprising the steps of contacting a biological sample derived from said animal with an immunologically interactive molecule of the present invention for a time and under conditions sufficient for a complex, such as an antigen:antibody complex, to form, and then detecting said complex formation.

A further aspect of the present invention contemplates a method of determining whether or not an animal has suffered from a past infection, or is currently infected, by Lawsonia intracellularis or a related microorganism, said method comprising contacting a tissue or fluid sample, such as blood or serum derived from said animal, with the immunogenic polypeptide of the invention for a time and under conditions sufficient for a complex, such as an antigen:antibody complex, to form, and then detecting said complex formation.

A further aspect of the present invention provides an isolated nucleic acid molecule which comprises a sequence of nucleotides that encodes, or is complementary to a nucleic acid molecule that encodes, a peptide, oligopeptide or polypeptide selected from the following:
  (i) a peptide, oligopeptide or polypeptide which comprises an amino acid sequence which has at least about 60% overall sequence identity to the amino acid sequence set forth in SEQ ID NO: 1;
  (ii) a peptide, oligopeptide or polypeptide which comprises at least about 5 contiguous amino acids derived from SEQ ID NO: 1; or
  (iii) a homologue, analogue or derivative of (i) or (ii), which mimics a B-cell or T-cell epitope of Lawsonia spp.

In a preferred embodiment, the isolated nucleic acid molecule comprises the nucleotide sequence set forth in SEQ ID NO: 2, or a degenerate variant thereof, or has at least about 60% sequence identity to all or a part thereof.

A still further aspect of the invention provides a diagnostic method of detecting Lawsonia intracellularis or related microorganism in a biological sample derived from an animal subject, said method comprising the steps of hybridising one or more polynucleotide or oligonucleotide probes or primers derived from the nucleotide sequence set forth in SEQ ID NO: 2 or a complementary nucleotide sequence thereof or a homologue, analogue or derivative thereof, to said sample, and then detecting said hybridisation using a detection means. The detection means according to this aspect of the invention is any nucleic acid-based hybridisation or amplification reaction.

A further aspect of the invention provides an isolated probe or primer derived from SEQ ID NO: 2 or a complementary nucleotide sequence thereto.

BRIEF DESCRIPTION OF THE DRAWINGS

Figure 3:
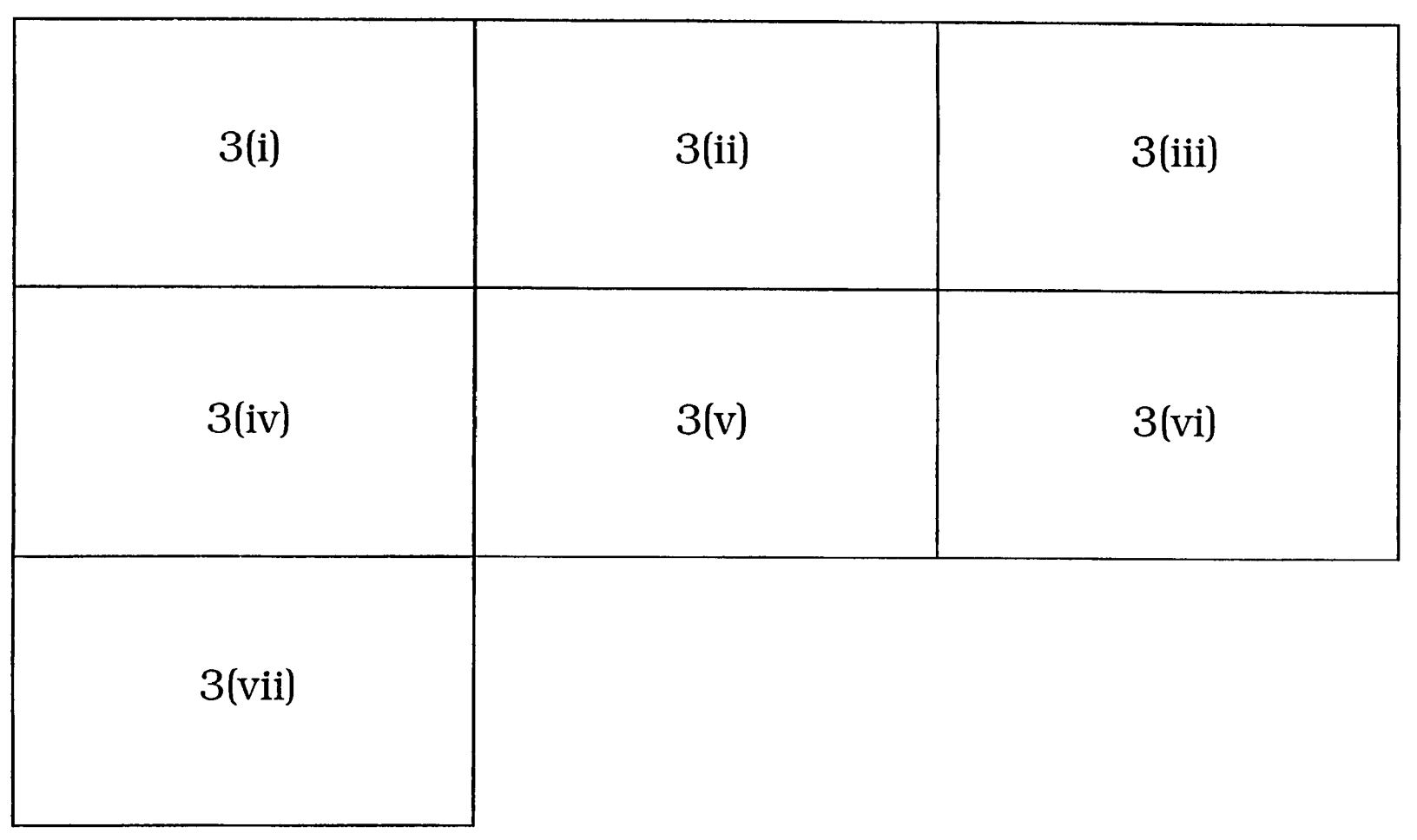
Figure 3II:
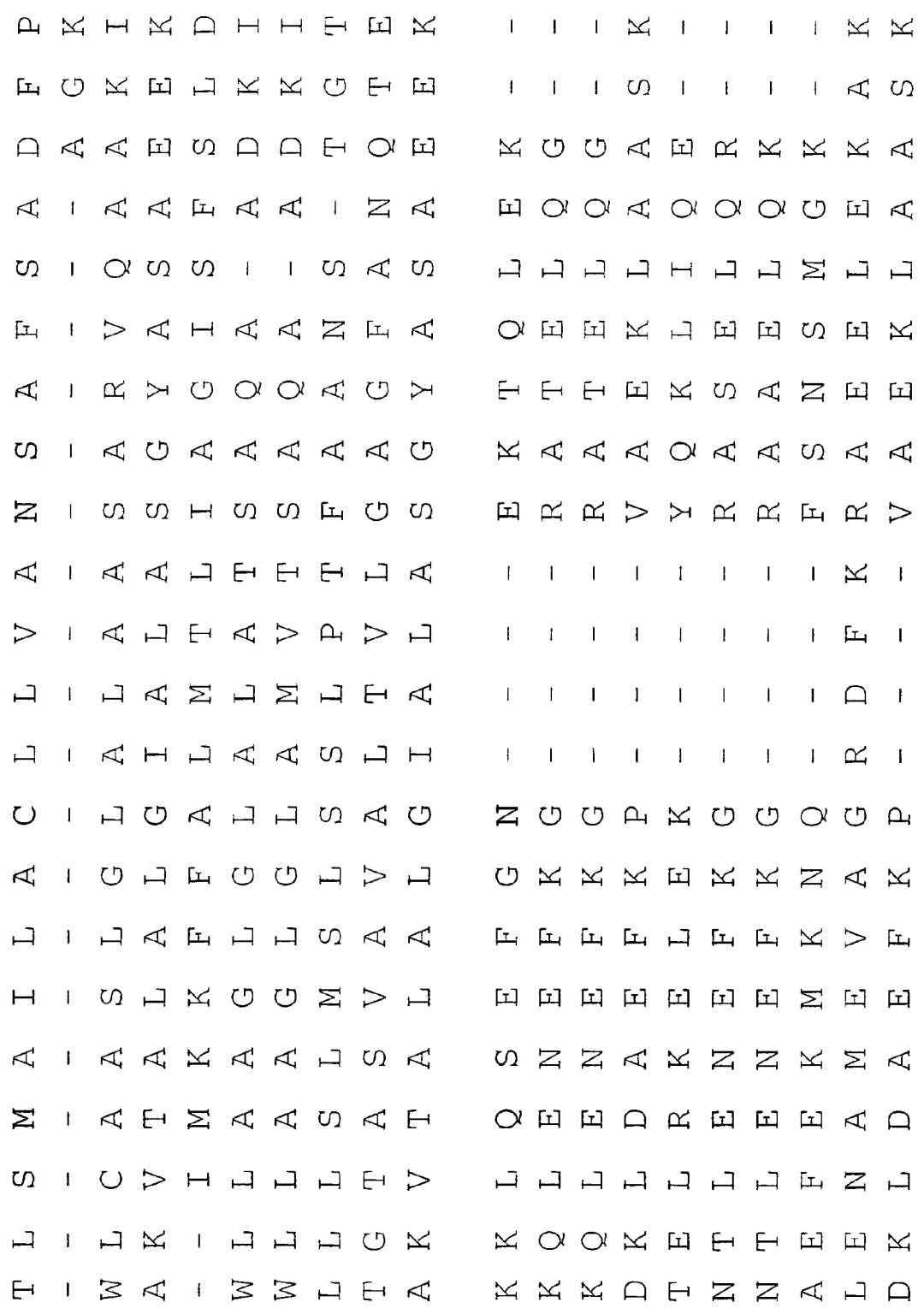
Figure 3III:
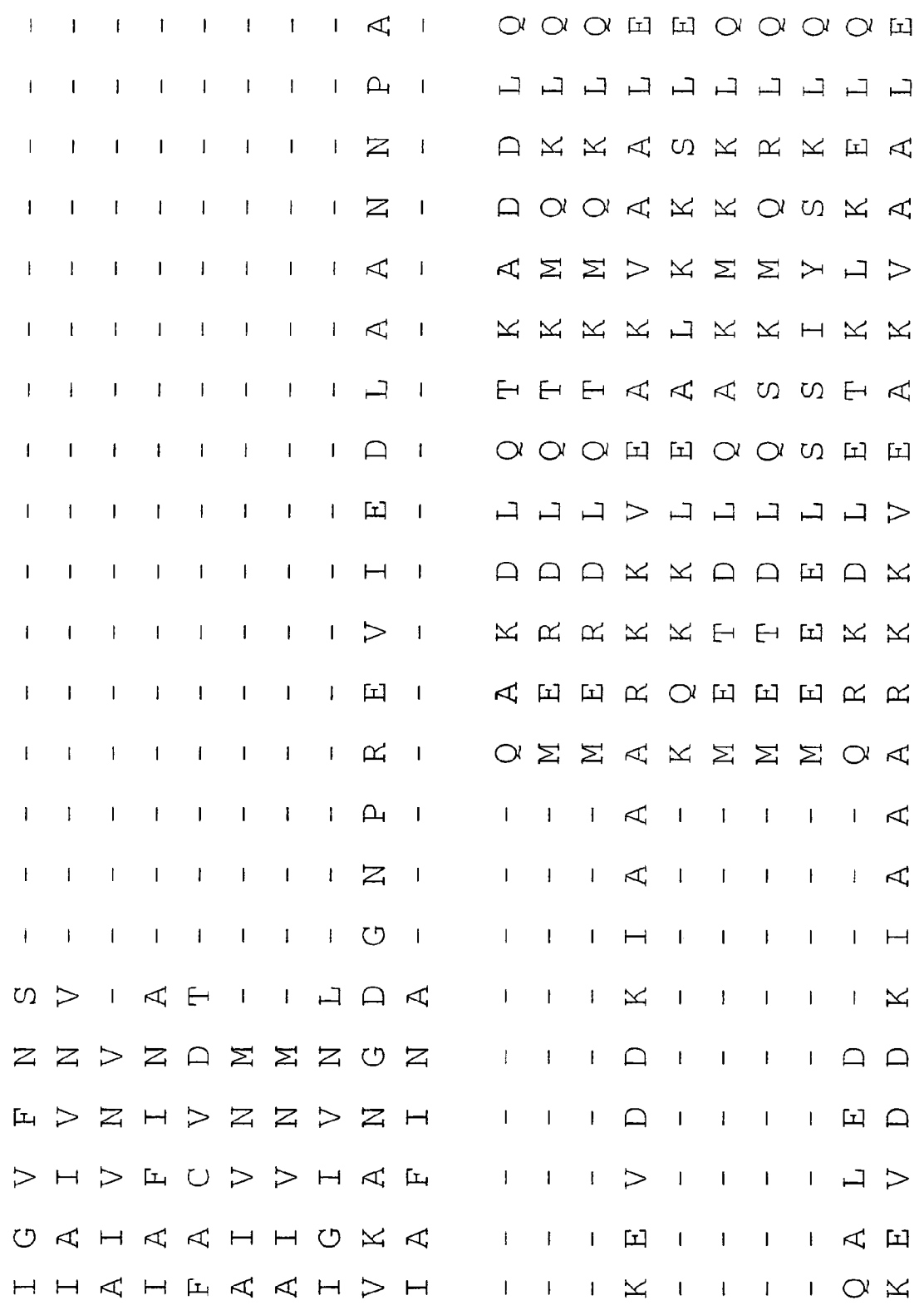
Figure 3IV:
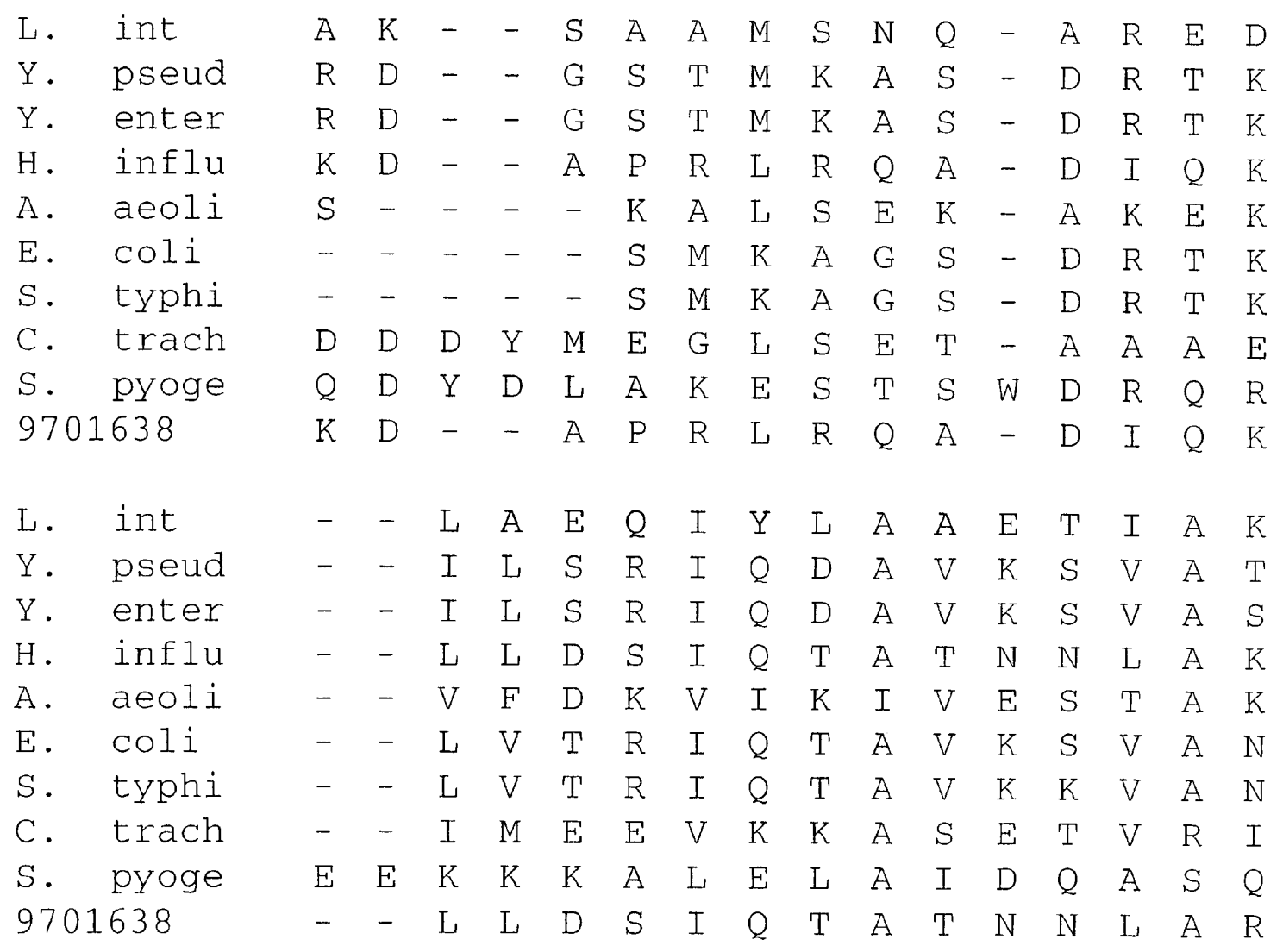
Figure 3V:
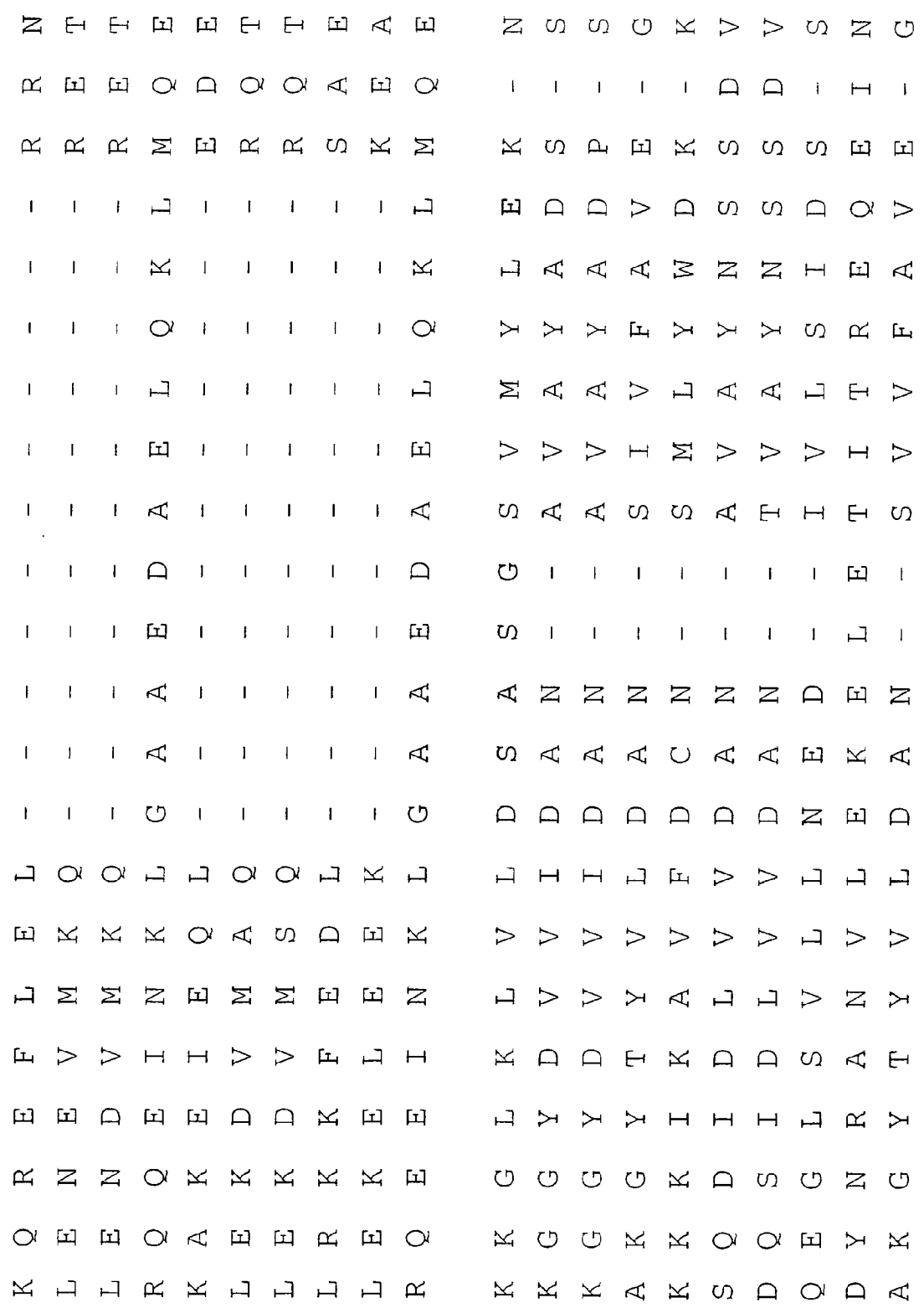
Figure 3VI:
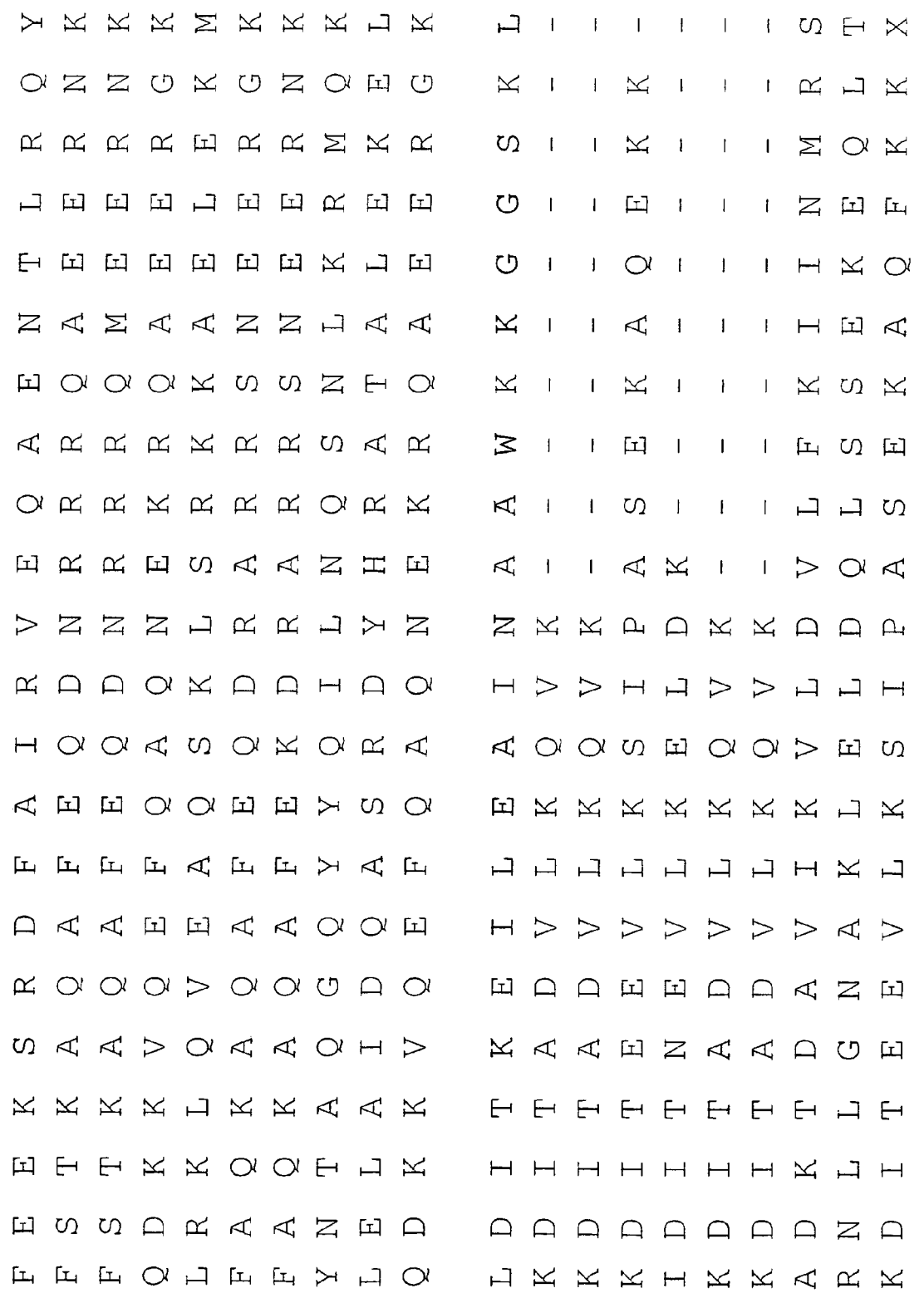

FIG. 3 is a schematic representation of an amino acid sequence alignment of various bacterial outer membrane H proteins. Amino acid sequences of OmpH from *Lawsonia intracellularis* (*L.int*) SEQ ID NO:1, *Yersinia pseudotuberculosis* (*Y. pseud*) SEQ ID NO:5, *Yersinia enterocolitica* (*Y. enter*) SEQ ID NO:6, *Haemophilus influenzae* (*H. influ*) SEQ ID NO:7, *Aquifex aeolicus* (*A. aeoli*) SEQ ID NO:8, *Escherician coli* (*E. coli*) SEQ ID NO:9, *Salmonella typhimurium* (*S. typhi*) SEQ ID NO:10, *Chlamydia trachomatis* (*C. trach*) SEQ ID NO:11, *Streptococcus pyogenes* (*S. pyoge*) SEQ ID NO:12 and Sequence 1 from International Patent Publication No. WO97/01638) SEQ ID NO: 13 are shown alligned with each other; gaps have been introduced to optimise alignment. Positions containing identical amino acid with respect to the OmpH sequence (SEQ ID NO:1) of *L. intracellularis* are shaded. Residues identical in all 10 sequences appear in boldface.

DETAILED DESCRIPTION OF THE INVENTION

Figure 1:
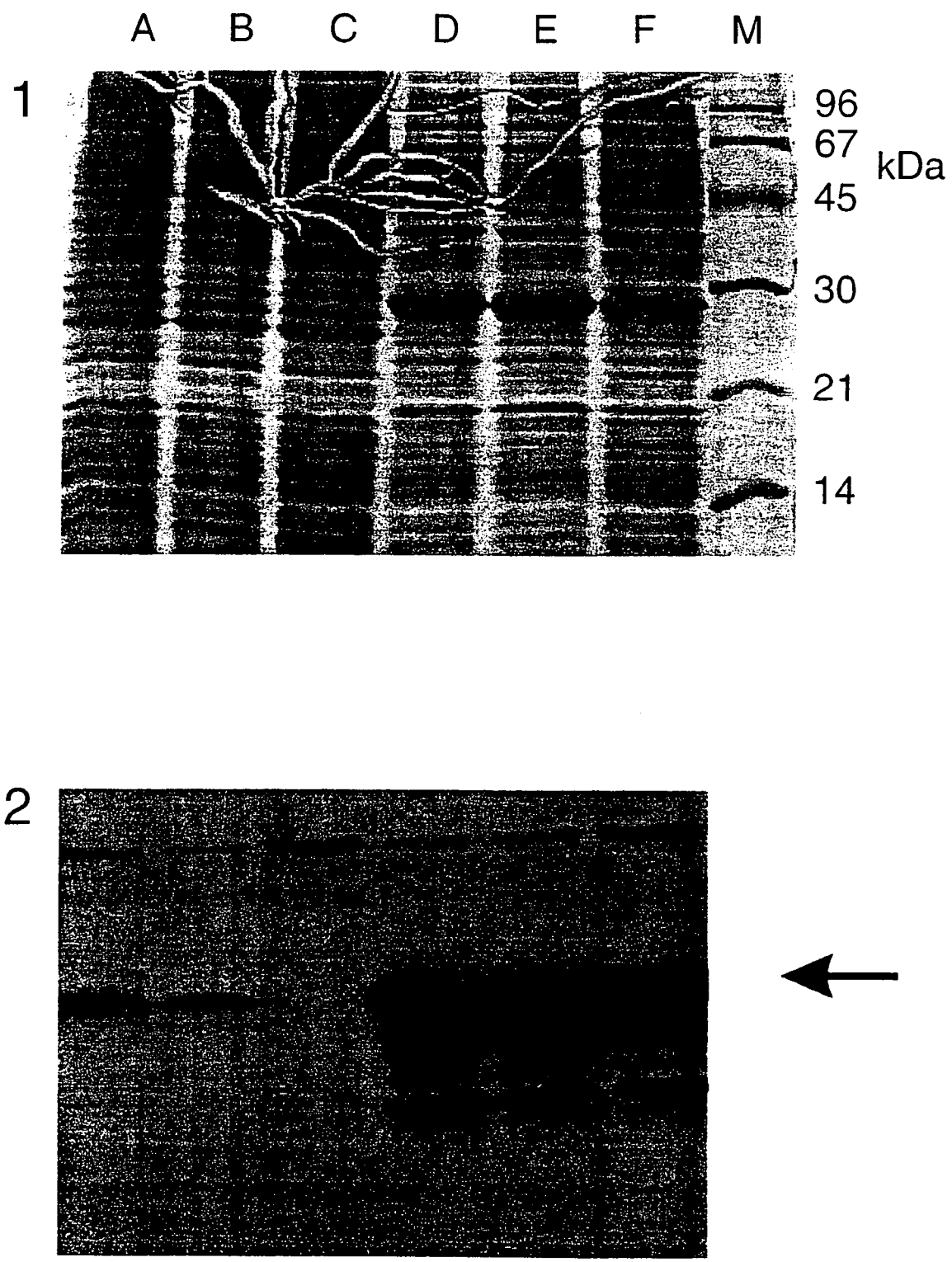
FIG. 1 is a copy of a photographic representation showing expression of recombinant *L. intracellularis* OmpH polypeptide from clone p97LI17. Induced and uninduced aliquots of protein derived from *E. coli* strains BL21 (pLysS) and BL21 (DE3) were separated on duplicate gels using SDS/PAGE. Gels were either stained with Coomassie Blue (top, gel 1) or transferred to nitrocellulose and probed using Y12 sera (gel, 2). The expressed immunogenic OmpH polypeptide is indicated by the arrow. Lanes A–C are p97LI17 grown in BL21(pLysS) following induction for 2 hours (lane A) or 1 hour (lane B) or without induction (lane C), Lanes D–F are p97LI17 grown in BL21(DE3) following induction for 2 hours (lane D) or 1 hour (lane E) or without induction (lane F). Lane M comprises the molecular weight standards, which are indicated in KDa at the right of gel 1.

In work leading up to the present invention, the inventors sought to identify immunogenic proteins of *Lawsonia intracellularis* for use in vaccines for the prophylaxis and treatment of PPE in animals, including pigs and birds.

Accordingly, one aspect of the present invention is directed to an isolated or recombinant immunogenic polypeptide which comprises, mimics or cross-reacts with a B-cell or T-cell epitope of the OmpH polypeptide derived from *Lawsonia* spp.

Epitopes of *Lawsonia* spp. may be B cell epitopes or T-cell epitopes. It is well-known that antibody-binding sites (B-cell epitopes) involve linear as well as conformational epitopes (van Regenmortel, 1992). B-cell epitopes are predominantly conformational. In contrast, T-cells recognize predominantly linear epitope sequences in combination with MHC class II molecules.

A precise identification and careful selection of epitopes of *Lawsonia* spp. facilitates the development of diagnostic reagents and vaccine compositions for the effective treatment or prophylaxis of *Lawsonia* infections. Epitope identification and characterization (i.e., determination of the molecular weight, amino acid sequence, and structure of epitopes of *Lawsonia* spp.) may be performed using art-recognised techniques. For the detection of conformational epitopes, degrading and denaturing of the epitope molecule must be avoided in order to conserve the three-dimensional structure, because the antigen-antibody reaction will be diminished if the secondary structure of the epitope is altered significantly. In practice, the characterisation and isolation of linear non-conformational epitopes is easier, because any immunoreactive regions are contained within a single peptide fragment or single amino acid sequence which is capable of being purified under a range of conditions.

Both non-conformational and conformational epitopes may be identified by virtue of their ability to bind detectable amounts of antibodies (such as IgM or IgG) from sera of animals immunised against or infected with *Lawsonia* spp. and, in particular *L. intracellularis*, or an isolated polypeptide derived therefrom or, alternatively, by virtue of their ability to bind detectable amounts of antibodies in a purified Ig fraction derived from such sera. The antibodies may be derived from or contained within pools of polyclonal sera, or may be monoclonal antibodies. Antibody fragments or recombinant antibodies, such as those expressed on the surface of a bacteriophage or virus particle, such as in a phage display library, may also be employed.

The determination of T-cell epitopes is performed by analysing the ability of the epitope peptides to induce the proliferation of peripheral blood lymphocytes or T-cell clones. The identification of T-cell epitopes is accomplished using a variety of methods as known in the art, including the use of whole and fragmented native or recombinant antigenic protein, as well as the more commonly employed "overlapping peptide" method. In the latter method, overlapping peptides which span the entire sequence of a polypeptide derived from *Lawsonia* spp. are synthesized and tested for their capacity to stimulate T-cell cytotoxic or proliferative responses in vitro.

Structure determination of both conformational non-linear and non-conformational linear epitopes may be performed by nuclear magnetic resonance spectroscopy (NMR) and X-ray crystallographic analysis. The determination of epitopes using X-ray techniques requires the protein-antibody complex to be crystallized, whereas NMR allows analysis of the complex in a liquid state. NMR measures the amount of amino acids as well as the neighbourhood of protons of different amino acid residues, wherein the alternating effect of two protons along the carbon backbone is characteristic of a particular epitope.

A successful method to recognize non-conformational linear epitopes is the immunoblot and in particular, the Western blot. Peptides may be generated from a complete *Lawsonia* spp. polypeptide by digestion with site-specific proteases, such as trypsin or chymotrypsin, and the peptides generated thereby can be separated using standard electrophoretic or chromatographic procedures. For example, after electrophoresis according to molecular weight using SDS/PAGE (SDS/polyacrylamide gel electrophoresis) and/or according to isoelectric point using IEF (isoelectric focussing) or alternatively, by two-dimensional electrophoresis, the peptides can be transferred to immobilizing nylon or nitrocellulose membranes and incubated with sera raised against the intact polypeptides. Peptides that comprise immunogenic regions (i.e., B-cell or T-cell epitopes) are bound by the antibodies in the sera and the bound antibodies may be detected using secondary antibodies, such as anti-IgG antibodies, that have been labelled radioactively or enzymatically. The epitopes may then be characterised by purification based upon their size, charge or ability to bind specifically to antibodies against the intact polypeptide, using one or more techniques, such as size-exclusion chromatography, ion-exchange chromatography, affinity chromatography or ELISA among others. After purification of the epitope, only one band or spot should be detectable with gel electrophoresis. The N-terminal or total sequencing of the peptide offers the possibility to compare the peptide with known proteins in databases.

Several computer-driven algorithms have now been devised to search for T-cell epitopes in proteins (Margalit et al, 1987; Vajda and C. DeLisi, 1990; Altuvia et al., 1995; Parker et al. 1994; De Groot et al., 1995; Gabriel et al, 1995; Meister et al., 1995). These algorithms search the amino acid sequence of a given protein for characteristics believed to be common to immunogenic peptides, locating regions that are likely to induce a cellular immune response in vitro. Computer-driven algorithms can identify regions of a *Lawsonia* spp. polypeptide that contain epitopes and are less variable among different isolates. Alternatively, computer-driven algorithms can rapidly identify regions of each isolate's more variable proteins that should be included in a multivalent vaccine.

The AMPHI algorithm (Margalit et al., 1987), which is based on the periodicity of T cell epitopes, has been widely used for the prediction of T-cell antigenic sites from sequence information alone. Essentially, AMPHI describes a common structural pattern of MHC binding motifs, since MHC binding motifs (i.e., patterns of amino acids that appear to be common to most of the peptides that bind to a specific MHC molecule) appear to exhibit the same periodicity as an alpha helix. Identification of T-cell epitopes by locating MHC binding motifs in an amino acid sequence provides an effective means of identifying immunogenic epitopes in diagnostic assays.

The EpiMer algorithm (Meister et al., 1995; Gabriel et al., 1995; DeGroot et al., 1995) locates clustered MHC binding motifs in amino acid sequences of proteins, based upon the correlation between MHC binding motif-dense regions and peptides that may have the capacity to bind to a variety of MHC molecules (promiscuous or multi-determinant binders) and to stimulate an immune response in these various MHC contexts as well (promiscuous or multi-determinant epitopes). The EpiMer algorithm uses a library of MHC binding motifs for multiple class I and class II HLA alleles to predict antigenic sites within a protein that have the potential to induce an immune response in subjects with a variety of genetic backgrounds. EpiMer locates matches to each MHC-binding motif within the primary sequence of a given protein antigen. The relative density of these motif matches is determined along the length of the antigen, resulting in the generation of a motif-density histogram. Finally, the algorithm identifies protein regions in this histogram with a motif match density above an algorithm-defined cutoff density value, and produces a list of subsequences representing these clustered, or motif-rich regions. The regions selected by EpiMer may be more likely to act as multi-determinant binding peptides than randomly chosen peptides from the same antigen, due to their concentration of MHC-binding motif matches. The selection of regions that are MHC binding motif-dense increases the likelihood that the predicted peptide contains a "valid" motif, and furthermore, that the reiteration of identical motifs may contribute to peptide binding.

Additional MHC binding motif-based algorithms have been described by Parker et al.(1994) and Altuvia et al. (1995). In these algorithms, binding to a given MHC molecule is predicted by a linear function of the residues at each position, based on empirically defined parameters, and in the case of the Altuvia et al.(1995) algorithm, known crystallographic structures may also be taken into consideration.

Recombinant methods offer the opportunity to obtain well characterized epitopes of high purity for the production of diagnostic reagents and epitope-specific vaccine formulations (Mohapatra et al., 1995). Based upon the amino acid sequence of a linear epitope and identification of the corresponding nucleotide sequence encoding same, polymerase chain reaction (PCR) may be performed to amplify the epitope-encoding region from cDNA. After cloning and expression in a suitable vector/host system, a large amount of epitopes of high purity can be extracted. Accordingly, the present invention clearly extends to both isolated non-recombinant polypeptides and recombinant polypeptides in an impure or isolated form.

The term "polypeptide" as used herein shall be taken to refer to any polymer consisting of amino acids linked by covalent bonds and includes within its scope full-length proteins and parts or fragments thereof such as, for example, oligopeptides and short peptide sequences consisting of at least about 5 amino acid residues, preferably at least about 10 amino acid residues, more preferably at least about 12 amino acid residues, and even more preferably at least about 15 amino acid residues.

Also included within the scope of the definition of a "polypeptide" are amino acid sequence variants, containing one or more preferably conservative amino acid substitutions, deletions, or insertions, which do not alter at least one essential property of said polypeptide such as, for example, its immunogenicity, use as a diagnostic reagent, or effectiveness as a peptide vaccine against *Lawsonia* spp, amongst others. Accordingly, a polypeptide may be isolated from a source in nature, or chemically synthesized. Furthermore, a polypeptide may be derived from a full-length protein by chemical or enzymatic cleavage, using reagents such as CNBr, trypsin, or chymotrypsin, amongst others.

Conservative amino acid substitutions are well-known in the art. For example, one or more amino acid residues of a native OmpH polypeptide of the invention can be substituted conservatively with an amino acid residue of similar charge, size or polarity, with the resulting polypeptide retaining an ability to function in a vaccine or as a diagnostic reagent as described herein. Rules for making such substitutions include those described by Dayhof (1978). More specifically, conservative amino acid substitutions are those that generally take place within a family of amino acids that are related in their side chains. Genetically-encoded amino acids are generally divided into four groups: (1) acidic=aspartate, glutamate; (2) basic=lysine, arginine, and histidine; (3) non-polar-alanine, valine, leucine, isoleucine, proline, phenylalanine, methionine, and tryptophan; and (4) uncharged polar=glycine, asparagine, glutamine, cysteine, serine, threonine, and tyrosine. Phenylalanine, tyrosine and tryptophan are also jointly classified as aromatic amino acids. One or more replacements within any particular group such as, for example, the substitution of leucine for isoleucine or valine or alternatively, the substitution of aspartate for glutamate or threonine for serine, or of any other amino acid residue with a structurally-related amino acid residue, will generally have an insignificant effect on the function of the resulting polypeptide.

The present invention is not limited by the source of the subject immunogen and clearly extends to isolated and recombinant polypeptides which are derived from a natural or a non-natural occurring source.

The term "recombinant polypeptide" as used herein shall be taken to refer to a polypeptide which is produced in vitro or in a host cell by the expression of a genetic sequence encoding said polypeptide, which genetic sequence is under the control of a suitable promoter, wherein a genetic manipulation has been performed in order to achieve said expression. Accordingly, the term "recombinant polypeptide" clearly encompasses polypeptides produced by the expression of genetic sequences contained in viral vectors, plasmids or cosmids that have been introduced into prokaryotic or eukaryotic cells, tissues or organs. Genetic manipulations which may be used in this context will be known to those skilled in the art and include, but are not limited to, nucleic acid isolation, restriction endonuclease digestion, exonuclease digestion, end-filling using the Klenow fragment of E. Coli DNA polymerase I or T4 DNA polymerase enzymes, blunt-ending of DNA molecules using T4 DNA polymerase or ExoIII enzymes, site-directed mutagenesis, ligation, and amplification reactions. As will be known to those skilled in the art, additional techniques such as nucleic acid hybridisations and nucleotide sequence analysis may also be utilised in the preparation of recombinant polypeptides, in confirming the identity of a nucleic acid molecule encoding a desired recombinant polypeptide and a genetic construct comprising the nucleic acid molecule.

Wherein the polypeptide of the present invention is a recombinant polypeptide, it may be produced in and, if desirable, isolated from a recombinant viral vector or host cell expression system. As will be known to those skilled in the relevant art, a cell for production of a recombinant polypeptide is selected on the basis of several parameters including the genetic constructs used to express the polypeptide under consideration, as well as the stability and activity of said polypeptide. It will also be known to those skilled in the art, that the stability or activity of a recombinant polypeptide may be determined, at least in part, by post-translational modifications to the polypeptide such as, for example, glycosylation, acylation or alkylation reactions, amongst others, which may vary between cell lines used to produce the recombinant polypeptide.

Accordingly, in a more particularly preferred embodiment, the present invention extends to a recombinant polypeptide or a derivative, homologue or analogue thereof as present in a virus particle, or as produced in prokaryotic or eukaryotic host cell, or in a virus or cell culture thereof.

The present invention also extends to a recombinant polypeptide according to any of the foregoing embodiments which is produced in a bacterial cell belonging to the genus Lawsonia, in particular a cell of L. intracellularis or a culture thereof.

The term "isolated polypeptide" refers to a polypeptide of the present invention which has been purified to some extent, preferably to at least about 20% by weight of protein, preferably to at least about 50% by weight of protein, more preferably to at least about 60% by weight of protein, still more preferably to at least about 70% by weight of protein and even more preferably to at least about 80% by weight of protein or greater, from its natural source or, in the case of non-naturally-occurring polypeptides, from the culture medium or cellular environment in which it was produced.

Such isolation may be performed to improve the immunogenicity of the polypeptide of the present invention, or to improve the specificity of the immune response against that polypeptide, or to remove toxic or undesirable contaminants therefrom. The necessary or required degree of purity of an isolated polypeptide will vary depending upon the purpose for which the polypeptide is intended, and for many applications it will be sufficient for the polypeptide preparation to contain no contaminants which would reduce the immunogenicity of the polypeptide when administered to a host animal, in particular a porcine or avian animal being immunized against PPE or, alternatively, which would inhibit immuno-specific binding in an immunoassay for the diagnosis of PPE or a causative agent thereof.

The purity of an isolated polypeptide of the present invention may be determined by any means known to those skilled in the art, including the degree of homogeneity of a protein preparation as assessed by SDS/polyacrylamide gel electrophoresis, 2-dimensional electrophoresis, or amino acid composition analysis or sequence analysis.

Preferably, the polypeptide of the present invention will be substantially homogeneous or substantially free of non-specific proteins, as assessed by SDS/polyacrylamide gel electrophoresis, 2-dimensional electrophoresis, or amino acid composition analysis or sequence analysis.

The polypeptide of the present invention can be purified for use as a component of a vaccine composition by any one or a combination of methods known to those of ordinary skill in the art, including, for example, reverse phase chromatography, HPLC, ion-exchange chromatography, and affinity chromatography, among others.

In a preferred embodiment, the isolated or recombinant polypeptide of the invention is immunologically cross-reactive with the L. intracellularis OmpH polypeptide exemplified herein.

In a further preferred embodiment, the isolated or recombinant polypeptide of the invention is derived from Lawsonia spp. and more preferably, the subject polypeptide is derived from Lawsonia intracellularis.

A B cell or T cell epitope of a polypeptide or a derivative, homologue or analogue thereof may comprise any combination of the following:
(i) the primary amino acid sequence of said region, known in the art as a continuous non-conformational epitope;
(ii) the secondary structure which said region adopts, known in the art as a continuous conformational epitope;
(iii) the tertiary structure which said region adopts in contact with another region of the same polypeptide molecule, known in the art as a discontinuous conformational epitope; or
(iv) the quaternary structure which said region adopts in contact with a region of another polypeptide molecule, known in the art as a discontinuous conformational epitope.

Accordingly, immunogenic polypeptides or derivatives, homologues or analogues thereof comprising the same, or substantially the same primary amino acid sequence are hereinafter defined as "immunogens which comprise a B cell or T cell epitope", or similar term.

Immunogenic polypeptides or derivatives, homologues, or analogues thereof comprising different primary amino acid sequences may comprise immunologically identical immunogens, because they possess conformational B cell or T cell epitopes that are recognised by the immune system of a host species to be identical. Such immunogenic polypeptides or derivatives, homologues or analogues thereof are hereinafter defined as "immunogens which mimic or cross-react with a B cell or T cell epitope", or similar term.

Accordingly, the present invention extends to an immunogen which comprises, mimics, or cross-reacts with a B-cell or T-cell epitope of an isolated or recombinant polypeptide according to any one of the foregoing embodiments or a derivative, homologue or analogue thereof. In a particularly preferred embodiment, the present invention provides an immunogen which comprises, mimics, or cross-reacts with a B-cell or T-cell epitope of an isolated or recombinant polypeptide which in its native form is obtainable from a species of *Lawsonia* such as, but not limited to *L. intracellularis* and which polypeptide preferably possesses OmpH activity.

Preferably, such immunogenic polypeptides will not comprise a primary amino acid sequence which is highly-conserved between *L. intracellularis* and another non-pathogenic microorganism which is normally resident in the gut or other organ of an animal, in particular a porcine or avian animal. The significance of this exclusion to those embodiments of the invention wherein specificity is essential to performance (eg vaccine and diagnostic applications) will be apparent to those skilled in the art.

To improve the immunogenicity of a subject polypeptide of the present invention one or more amino acids not corresponding to the original protein sequence can be added to the amino or carboxyl terminus of the polypeptide. Such extra amino acids are useful for coupling the polypeptide to another peptide or polypeptide, to a large carrier protein or to a solid support. Amino acids that are useful for these purposes include but are not limited to tyrosine, lysine, glutamic acid, aspartic acid, cysteine and derivatives thereof. Additional protein modification techniques can be used such as, e.g., $NH_2$-acetylation or COOH-terminal amidation, to provide additional means for coupling the polypeptide to another polypeptide, protein, or peptide molecule, or to a solid support. Procedures for coupling polypeptides to each other, or to carrier proteins or solid supports, are well known in the art. Polypeptides containing the above-mentioned extra amino acid residues at either the carboxyl- or amino-termini and either uncoupled or coupled to a carrier or solid support, are consequently within the scope of the present invention.

Furthermore, the polypeptide can be immobilised to a polymeric carrier or support material.

In an alternative embodiment, the immunogenicity of a polypeptide of the present invention may be improved using molecular biology techniques to produce a fusion protein containing one or more polypeptides of the present invention fused to a carrier molecules such as a highly immunogenic protein.

For example, a fusion protein containing a polypeptide of the present invention fused to the highly immunogenic B subunit of cholera toxin can be used to increase the immune response to the polypeptide. The present invention also contemplates fusion proteins comprising a cytokine, such as an interleukin, fused to the subject polypeptide of the present invention and genes encoding same.

Preferably, the polypeptide of the present invention, or a derivative, homologue or analogue thereof, when administered to a mammal, induces an immune response in said mammal. More preferably, the polypeptide of the present invention, when administered to a mammal, in particular a porcine animal (e.g., a pig) induces a protective immune response against *Lawsonia* spp., and preferably against *L. intracellularis*, therein. As used herein, the phrase "induction of a protective immune response", and the like, refers to the ability of the administered polypeptide of the present invention to prevent or detectably slow the onset, development, or progression of symptoms associated with *Lawsonia* infection, and preferably, to prevent or detectably slow the onset, development, or progression of symptoms associated with PPE in pigs.

Preferably, the immunogenic polypeptide of the invention comprises an amino acid sequence which is substantially the same as the amino acid sequence set forth in SEQ ID NO: 1 or is at least about 60% identical overall to SEQ ID NO: 1, or is at least about 75% identical to at least 8 contiguous amino acids of SEQ ID NO: 1. In a preferred embodiment, the immunogenic polypeptide of the present invention consists essentially of the amino acid sequence of SEQ ID NO:1 or the amino acid sequence encoded by the OmpH-encoding nucleotide sequence present in pALK13 (ATCC 207196).

For the purposes of nomenclature, the amino acid sequence set forth in SEQ ID NO: 1 represents the amino acid sequence of the OmpH polypeptide encoded by the *Lawsonia intracellularis* ompH gene. The nucleotide sequence of the *L. intracellularis* ompH gene is set forth in SEQ ID NO: 2.

Preferably, the percentage amino acid sequence identity to SEQ ID NO: 1 is at least about 70%, more preferably at least about 80%, even more preferably at least about 90%, and still even more preferably at least about 95%.

In determining whether or not two amino acid sequences fall within these percentage limits, those skilled in the art will be aware that it is necessary to conduct a side-by-side comparison or multiple alignment of sequences. In such comparisons or alignments, differences will arise in the positioning of non-identical residues, depending upon the algorithm used to perform the alignment. In the present context, reference to a percentage sequence identity or similarity between two or more amino acid sequences shall be taken to refer to the number of identical and similar residues respectively, between said sequences as determined using any standard algorithm known to those skilled in the art. For example, amino acid sequence identities or similarities may be calculated using the GAP programme of the Computer Genetics Group, Inc., University Research Park, Madison, Wis., United States of America (Devereaux et al, 1984). The GAP programme utilizes the algorithm of Needleman and Wunsch (1970) to maximise the number of identical/similar residues and to minimise the number and/or length of sequence gaps in the alignment. Alternatively or in addition, where more than two amino acid sequences are being compared, the ClustalW programme of Thompson et al (1994) can be used.

In an alternative embodiment, the present invention provides an isolated or recombinant immunogenic polypeptide which comprises, mimics or cross-reacts with a B-cell or T-cell epitope of the OmpH polypeptide derived from *Lawsonia* spp. wherein said isolated or recombinant immunogenic polypeptide comprises an amino acid sequence which comprises at least 5 contiguous amino acid residues of SEQ ID NO: 1 or a homologue, analogue or derivative thereof.

Preferably, the isolated or recombinant immunogenic polypeptide of the invention comprises at least about 10 contiguous amino acids derived from SEQ ID NO: 1, more preferably at least about 20 contiguous amino acid residues derived from SEQ ID NO: 1, even more preferably at least about 30 contiguous amino acid residues derived from SEQ ID NO: 1 and still even more preferably at least about 40 contiguous amino acid residues derived from SEQ ID NO: 1.

The present invention further encompasses homologues, analogues and derivatives of a polypeptide comprising the amino acid sequence set forth in SEQ ID NO: 1. "Homologues" of a polypeptide are those polypeptides which contain amino acid substitutions, deletions and/or additions relative to the polypeptide without altering one or more of its properties, such as its immunogenicity, biological activity or catalytic activity. In such molecules, amino acids can be replaced by other amino acids having similar properties such as, for example, hydrophobicity, hydrophilicity, hydrophobic moment, antigenicity, propensity to form or break α-helical structures or β-sheet structures, and so on.

Substitutional variants are those in which at least one residue in the sequence has been removed and a different residue inserted in its place. Amino acid substitutions are typically of single residues, but may be clustered depending upon functional constraints placed upon the polypeptide; insertions will usually be of the order of about 1–10 amino acid residues and deletions will range from about 1–20 residues. Preferably, amino acid substitutions will comprise conservative amino acid substitutions, such as those described supra.

Insertional amino acid sequence variants are those in which one or more amino acid residues are introduced into a predetermined site in the protein. Insertions can comprise amino-terminal and/or carboxyl terminal fusions as well as intra-sequence insertions of single or multiple amino acids. Generally, insertions within the amino acid sequence will be smaller than amino or carboxyl terminal fusions, of the order of about 1 to 4 residues.

Deletional variants are characterised by the removal of one or more amino acids from the sequence.

Amino acid variants of the polypeptide of the present invention may readily be made using peptide synthetic techniques well known in the art, such as solid phase peptide synthesis and the like, or by recombinant DNA manipulations. The manipulation of DNA sequences to produce variant proteins which manifest as substitutional, insertional or deletional variants are well known in the art. For example, techniques for making substitution mutations at predetermined sites in DNA having known sequence are well known to those skilled in the art, such as by M13 mutagenesis or other site-directed mutagenesis protocol.

"Analogues" are defined as peptides, oligopeptides and polypeptides which are functionally equivalent to the peptides of the present invention but which contain certain non-naturally occurring or modified amino acid residues as will be known to those skilled in the art. Accordingly, an "analogue" as defined herein need not comprise an amino acid sequence which is similar to the amino acid sequence set forth herein such as, for example, peptides, oligopeptides and polypeptides which are derived from computational predictions or empirical data revealing the secondary, tertiary or quaternary structure of the polypeptide of the present invention, and which therefore do not comprise the same primary amino acid sequence of said polypeptide, yet nevertheless mimic or cross-react with B-cell or T-cell epitope of *Lawsonia* spp. and preferably, mimic or cross-react with B-cell or T-cell epitope of *Lawsonia intracellularis*.

For example, mimotopes (polypeptide analogues that cross-react with a B-cell or T-cell epitope of the *Lawsonia* polypeptide of the invention but, however, comprise a different amino acid sequence to said epitope) may be identified by screening random amino acid sequences in peptide libraries with antibodies that bind to a desired T-cell or B-cell epitope. As with techniques for the identification of B-cell or T-cell epitopes as described supra, the antibodies used to identify such mimotopes may be polyclonal or monoclonal or recombinant antibodies, in crude or purified form. Mimotopes of a T-cell epitope may then be assayed further for their ability to stimulate T-cell cytotoxic or proliferative responses in vitro. Mimotopes are particularly useful as analogues of non-linear (i.e., conformational) epitopes of the polypeptide of the present invention, because conformational epitopes are generally formed from non-contiguous regions in a polypeptide, and the mimotopes provide immunogenic equivalents thereof in the form of a single peptide molecule.

Additionally, the use of polypeptide analogues can result in polypeptides with increased immunogenic and/or antigenic activity, that are less sensitive to enzymatic degradation, and which are more selective. A suitable proline analogue is 2-aminocyclopentane carboxylic acid ($\beta AC^5c$) which has been shown to increase the immunogenic activity of a native polypeptide more than 20 times (Mierke et al, 1990; Portoghese et al, 1990; Goodman et al, 1987).

"Derivatives" of a polypeptide described herein are those peptides, oligopeptides and polypeptides which comprise at least about five contiguous amino acid residues of the amino acid sequence set forth in SEQ ID NO: 1. A "derivative" may further comprise additional naturally-occurring, altered glycosylated, acylated or non-naturally occurring amino acid residues compared to the amino acid sequence set forth in SEQ ID NO: 1. Alternatively or in addition, a derivative may comprise one or more non-amino acid substituents such as, for example, a reporter molecule or other ligand, covalently or non-covalently bound to the amino acid sequence such as, for example, a reporter molecule which is bound thereto to facilitate its detection.

Other examples of recombinant or synthetic mutants and derivatives of the peptide immunogens of the present invention include those incorporating single or multiple substitutions, deletions and/or additions therein, such as carbohydrates, lipids and/or proteins or polypeptides. Naturally occurring or altered glycosylated or acylated forms of the subject peptides are particularly contemplated by the present invention. Additionally, homopolymers or heteropolymers comprising one or more copies of the subject peptide listed in SEQ ID NO: 1, or one or more derivatives, homologues or analogues thereof, are within the scope of the invention.

Preferably, homologues, analogues and derivatives of the polypeptide of the invention are "immunogenic", defined hereinafter as the ability of said polypeptide, or a derivative, homologue or analogue thereof, to elicit B cell and/or T cell responses in the host, in response to immunization.

Preferred homologues, analogues and derivatives of the amino acid sequence set forth in SEQ ID NO: 1 include those amino acid variants that function as B cell or T cell epitopes of said amino acid sequence which are capable of mediating an immune response such as, for example, mimotopes of the immunogenic polypeptide described herein which have been produced by synthetic means, such as by Fmoc chemistry. The only requirement of such molecules is that they cross-react immunologically with a polypeptide which comprises the amino acid sequence set forth in SEQ ID NO: 1 or a derivative thereof which comprises at least 5 contiguous amino acids in length of SEQ ID NO: 1.

As will be apparent to those skilled in the art, such homologues, analogues and derivatives of the polypeptide of the invention molecules will be useful to prepare antibodies that cross-react with antibodies against said polypeptide and/or to elicit a protective immune response of similar specificity to that elicited by said polypeptide. Such molecules will also be useful in diagnostic and other applications that are immunological in nature such as, for example, diagnostics which utilise one or more immunoassay formats (eg. ELISA, RIA and the like).

Accordingly, the immunogen of the present invention or a derivative, homologue or analogue thereof is useful in vaccine compositions that protect an individual against infection by *L. intracellularis* and/or as an antigen to elicit polyclonal or monoclonal antibody production and/or in the detection of antibodies against *L. intracellularis* in infected animals, particularly in porcine and avian animals.

The present inventors have also shown that the N-terminal region of SEQ ID NO: 1 and the C-terminal 15–50 amino acid residues of SEQ ID NO: 1 are particularly unique, as compared to other immunogenic amino acid sequences, including those of the OmpH polypeptides of other animal pathogens (FIG. 3). Accordingly, peptides, oligopeptides and polypeptides which comprise such unique epitope regions of SEQ ID NO: 1, will have improved specificity compared to other regions of the *Lawsonia* spp. OmpH molecule. The particular advantages of such peptides will be immediately apparent to those skilled in the production of vaccine compositions, where specificity against a pathogen of interest is an important consideration.

The present inventors have shown that the *Lawsonia intracellularis* OmpH polypeptide set forth in SEQ ID NO: 1 and, in particular the C-terminal 15 amino acid residues of SEQ ID NO: 1, is not highly conserved, as compared to the corresponding region of the OmpH polypeptides derived from *Yersinia* spp. and *Haemophilus influenzae*. Accordingly, the *L. intracellularis* OmpH polypeptide and/or the C-terminal 15 amino acid residues thereof, is a promising antigenic peptide for the formulation of *Lawsonia*-specific vaccines and diagnostics for the specific detection of *Lawsonia* spp. in biological samples.

A second aspect of the present invention provides a vaccine composition for the prophylaxis or treatment of infection in a mammal or bird by *L. intracellularis* or similar or otherwise related microorganism, said vaccine composition comprising:
  (i) an immunogenic component which comprises an isolated or recombinant polypeptide having at least about 60% overall amino acid sequence identity to the amino acid sequence set forth in SEQ ID NO: 1 and/or comprising at least 5 contiguous amino acids derived from SEQ ID NO: 1 or an immunogenic homologue, analogue or derivative thereof which is immunologically cross-reactive with *Lawsonia intracellularis*; and
  (ii) one or more carriers, diluents and/or adjuvants suitable for veterinary or pharmaceutical use.

As used herein, the term "immunogenic component" refers to a peptide, polypeptide or a protein encoded by DNA from, or derived from, *L. intracellularis* or a related microorganism thereto which is capable of inducing a protective immune response in an animal, in particular a porcine or avian animal, whether or not said peptide, polypeptide or protein is in an isolated or recombinant form. Accordingly, the vaccine composition clearly encompasses those vaccine compositions which comprise attenuated, killed or non-pathogenic isolates or forms of *L. intracellularis* or related microorganisms thereto which comprise or express said peptide, polypeptide or protein.

By "protective immune response" is meant that the immunogenic component elicits an immune response in the animal to which the vaccine composition is administered at the humoral and/or cellular level which is sufficient to prevent infection by *Lawsonia intracellularis* or a related microorganism thereto and/or which is sufficient to detectably reduce one or more symptoms or conditions, or to detectably slow the onset of one or more symptoms or conditions, associated with infection by *Lawsonia intracellularis* or a related microorganism thereto in an animal host, as compared to a control infected animal. The term "effective amount" of an immunogenic component present in the vaccine composition refers to that amount of said immunogenic component that is capable of inducing a protective immune response after a single complete dose has been administered, or after several divided doses have been administered.

Preferably, the polypeptide component of the subject vaccine composition comprises an amino acid sequence which is both immunogenic and specific, by virtue of its immunological cross-reactivity with the causative agent of PPE, *Lawsonia intracellularis*. In this regard, it will be apparent from the preceding description that such polypeptide components may comprise an amino acid sequence derived from SEQ ID NO: 1 or a homologue, analogue or derivative of the amino acid sequence set forth in SEQ ID NO: 1 such as, for example, a mimotope of said sequence.

The immunogenic polypeptide or immunogenic homologue, analogue or derivative may be a naturally-occurring peptide, oligopeptide or polypeptide in isolated or recombinant form according to any of the embodiments described supra or exemplified herein. Preferably, the immunogenic polypeptide or immunogenic homologue, analogue or derivative is derived from *Lawsonia* spp., in particular *L. intracellularis* or a microorganism that is related thereto.

Preferably, the immunogenic component has undergone at least one purification step or at least partial concentration from a cell culture comprising *L. intracellularis* or a related microorganism thereto, or from a lysed preparation of *L. intracellularis* cells or related microorganism, or from another culture in which the immunogenic component is recombinantly expressed. The purity of such a component which has the requisite immunogenic properties is preferably at least about 20% by weight of protein in a particular preparation, more preferably at least about 50%, even more preferably at least about 60%, still more preferably at least about 70% and even more preferably at least about 80% or greater.

The immunogenic component of the vaccine of the present invention can comprise a single peptide, polypeptide or protein, or a range or combination of different peptides, polypeptides or proteins covering different or similar epitopes. In addition or, alternatively, a single polypeptide can be provided with multiple epitopes. The latter type of vaccine is referred to as a polyvalent vaccine. A multiple epitope includes two or more epitopes located within a peptide or polypeptide molecule.

The formulation of vaccines is generally known in the art and reference can conveniently be made to Remington's Pharmaceutical Sciences, 17th ed., Mack Publishing Co., Easton, Pa., USA.

A particularly useful form of the vaccine is a recombinant vaccine produced, for example, in a vaccine vector, such as but not limited to a all transfected with a vaccinia virus vector or a bacterial cell capable of expressing the immunogenic component.

The present invention clearly extends to recombinant vaccine compositions in which the immunogenic component at least is contained within killed vaccine vectors prepared, for example, by heat, formalin or other chemical treatment, electric shock or high or low pressure forces. According to this embodiment, the immunogenic component of the vaccine is generally synthesized in a live vaccine vector which is killed prior to administration to an animal.

Furthermore, the vaccine vector expressing the immunogenic component may be non-pathogenic or attenuated. Within the scope of this embodiment are cells that have been transfected with non-pathogenic or attenuated viruses encoding the immunogenic component of the vaccine and non-pathogenic or attenuated cells that directly express the immunogenic component.

Attenuated or non-pathogenic host cells include those cells which are not harmful to an animal to which the subject vaccine is administered. As will be known to those skilled in the art, "live vaccines" can comprise an attenuated virus vector encoding the immunogenic component or a host cell comprising same, which is capable of replicating in an animal to which it is administered and using host cell machinery to express the immunogenic component, albeit producing no adverse side-effects therein. Such vaccine vectors may colonise the gut or other organ of the vaccinated animal. Such live vaccine vectors are efficacious by virtue of their ability to continually express the immunogenic component in the host animal for a time and at a level sufficient to confer protective immunity against a pathogen which expresses an immunogenic equivalent of said immunogenic component. The present invention clearly encompasses the use of such attenuated or non-pathogenic vectors and live vaccine preparations.

The vaccine vector may be a virus, bacterial cell or a eukaryotic cell such as an avian, porcine or other mammalian cell or a yeast cell or a cell line such as COS, VERO, HeLa, mouse C127, Chinese hamster ovary (CHO), WI-38, baby hamster kidney (BHK) or MDCK cell lines. Suitable prokaryotic cells include *Mycobacterium* spp., *Corynebacterium* spp., *Salmonella* spp., *Escherichia coli*, *Bacillus* spp. and *Pseudomonas* spp, amongst others. Bacterial strains which are suitable for the present purpose are well-known in the relevant art (Ausubel et al, 1987; Sambrook et al, 1989).

Such cells and cell lines are capable of expression of a genetic sequence encoding an OmpH peptide, polypeptide or protein of the present invention from *L. intracellularis* in a manner effective to induce a protective immune response in the animal. For example, a non-pathogenic bacterium could be prepared containing a recombinant sequence capable of encoding a peptide, polypeptide or protein from *L. intracellularis*. The recombinant sequence would be in the form of an expression vector under the control of a constitutive or inducible promoter. The bacterium would then be permitted to colonise suitable locations in a pig's gut and would be permitted to grow and produce the recombinant peptide, polypeptide or protein in amount sufficient to induce a protective immune response against *L. intracellularis*.

In a further alternative embodiment, the vaccine can be a DNA or RNA vaccine comprising a DNA or RNA molecule encoding a peptide, polypeptide or protein of the present invention which is injected into muscular tissue or other suitable tissue in a pig under conditions sufficient to permit transient expression of said DNA or RNA to produce an amount of peptide, polypeptide or protein effective to induce a protective immune response. In a preferred embodiment, the DNA vaccine is in the form of a plasmid, in which the DNA is operably connected with a promoter region capable of expressing the nucleotide sequence encoding the immunogen in cells of the immunized animal.

In the production of a recombinant vaccine, except for a DNA vaccine described herein, it is therefore necessary to express the immunogenic component in a suitable vector system. For the present purpose, the immunogenic component can be expressed by:

(i) placing an isolated nucleic acid molecule in an expressible format, said nucleic acid molecule comprising the coding region of the nucleotide sequence set forth in SEQ ID NO: 2 or a protein-encoding homologue, analogue or derivative of SEQ ID NO: 2 selected from the group consisting of:
   (a) nucleotide sequences that have at least about 60% sequence identity to SEQ ID NO: 2;
   (b) nucleotide sequences that hybridise under at least low stringency hybridisation, preferably at least moderate stringency conditions, and even more preferably under high stringency conditions, to the complement of SEQ ID NO: 2; and
   (c) nucleotide sequences that encode the amino acid sequence set forth in SEQ ID NO: 1 or a homologue, analogue or derivative thereof, including, for example, a mimotope of the amino acid set forth in SEQ ID NO: 1;
(ii) introducing the isolated nucleic acid molecule of (i) in an expressible format into a suitable vaccine vector; and
(iii) incubating or growing the vaccine vector for a time and under conditions sufficient for expression of the immunogenic component encoded by said nucleic acid molecule to occur.

For the purposes of defining the level of stringency, a low stringency is defined herein as being a hybridisation and/or a wash carried out in 6×SSC buffer, 0.1% (w/v) SDS at 28° C. A moderate stringency is defined herein as being a hybridisation and/or washing carried out in 2×SSC buffer, 0.1% (w/v) SDS at a temperature in the range 45° C. to 65° C. A high stringency is defined herein as being a hybridisation and/or wash carried out in 0.1×SSC buffer, 0.1% (w/v) SDS at a temperature of at least 65° C.

Generally, the stringency is increased by reducing the concentration of SSC buffer, and/or increasing the concentration of SDS and/or increasing the temperature of the hybridisation and/or wash. Those skilled in the art will be aware that the conditions for hybridisation and/or wash may vary depending upon the nature of the hybridisation membrane or the type of hybridisation probe used. Conditions for hybridisations and washes are well understood by one normally skilled in the art. For the purposes of clarification of the parameters affecting hybridisation between nucleic acid molecules, reference is found in pages 2.10.8 to 2.10.16. of Ausubel et al. (1987), which is herein incorporated by reference.

As used herein, a "nucleic acid molecule in an expressible format" is a protein-encoding region of a nucleic acid molecule placed in operable connection with a promoter or other regulatory sequence capable of regulating expression in the vaccine vector system.

Reference herein to a "promoter" is to be taken in its broadest context and includes the transcriptional regulatory sequences of a classical genomic gene, including the TATA box which is required for accurate transcription initiation, with or without a CCAAT box sequence and additional regulatory elements (i.e., upstream activating sequences, enhancers and silencers) which alter gene expression in response to developmental and/or external stimuli, or in a tissue-specific manner. In the present context, the term "promoter" is also used to describe a recombinant, synthetic or fusion molecule, or derivative which confers, activates or enhances the expression of a nucleic acid molecule to which it is operably connected, and which encodes the immunogenic polypeptide. Preferred promoters can contain additional copies of one or more specific regulatory elements to further enhance expression and/or to alter the spatial expression and/or temporal expression of the said nucleic acid molecule.

Placing a nucleic acid molecule under the regulatory control of i.e., "in operable connection with" a promoter sequence means positioning the said molecule such that expression is controlled by the promoter sequence. Promoters are generally, but not necessarily, positioned 5' (upstream) to the genes that they control. In the construction of heterologous promoter/structural gene combinations it is generally preferred to position the promoter at a distance from the gene transcription start site that is approximately the same as the distance between that promoter and the gene it controls in its natural setting, i.e., the gene from which the promoter is derived. Furthermore, the regulatory elements comprising a promoter are usually positioned within 2 kb of the start site of transcription of the gene. As is known in the art, some variation in this distance can be accommodated without loss of promoter function. Similarly, the preferred positioning of a regulatory sequence element with respect to a heterologous gene to be placed under its control is defined by the positioning of the element in its natural setting, i.e., the genes from which it is derived. Again, as is known in the art, some variation in this distance can also occur.

The prerequisite for producing intact polypeptides in bacteria such as $E.\ coli$ is the use of a strong promoter with an effective ribosome binding site. Typical promoters suitable for expression in bacterial cells such as $E.\ coli$ include, but are not limited to, the lacz promoter, temperature-sensitive $\lambda_L$ or $\lambda_R$ promoters, T7 promoter or the IPTG-inducible tac promoter. A number of other vector systems for expressing the nucleic acid molecule of the invention in $E.\ coli$ are well-known in the art and are described, for example, in Ausubel et al (1987) or Sambrook et al (1989). Numerous plasmids with suitable promoter sequences for expression in bacteria and efficient ribosome binding sites have been described, such as for example, pKC30 ($\lambda_L$: Shimatake and Rosenberg, 1981), pKK173-3 (tac: Amann and Brosius, 1985), pET-3 (T7: Studier and Moffat, 1986), the pFLEX series of expression vectors (Pfizer Inc., CT, USA) or the pQE series of expression vectors (Qiagen, CA), amongst others. Typical promoters suitable for expression in viruses of eukaryotic cells and eukaryotic cells include the SV40 late promoter, SV40 early promoter and cytomegalovirus (CMV) promoter, CMV IE (cytomegalovirus immediate early) promoter amongst others.

Means for introducing the isolated nucleic acid molecule or a genetic construct comprising same into a cell for expression of the immunogenic component of the vaccine composition are well-known to those skilled in the art. The technique used for a given organism depends on the known successful techniques. Means for introducing recombinant DNA into animal cells include microinjection, transfection mediated by DEAE-dextran, transfection mediated by liposomes such as by using lipofectamine (Gibco, MD, USA) and/or cellfectin (Gibco, MD, USA), PEG-mediated DNA uptake, electroporation and microparticle bombardment such as by using DNA-coated tungsten or gold particles (Agracetus Inc., WI, USA) amongst others.

The immunogenic component of a vaccine composition as contemplated herein exhibits excellent therapeutic activity, for example, in the treatment and/or prophylaxis of PPE when administered in an amount which depends on the particular case. For example, for recombinant peptide molecules, from about 0.5 µg to about 20 mg may be administered, preferably from about 1 µg to about 10 mg, more preferably from about 10 µg to about 5 mg, and most preferably from about 50 µg to about 1 mg equivalent of the immunogenic component in a volume of about 1 ml to about 5 ml. For DNA vaccines, a preferred amount is from about 1 µg to about 10 mg in a volume of about 1 to 5 ml. The DNA can be present in "naked" form or it can be administered together with an agent facilitating cellular uptake (e.g., in liposomes or cationic lipids). The important feature is to administer sufficient immunogen to induce a protective immune response. The above amounts can be administered as stated or calculated per kilogram of body weight. Dosage regime can be adjusted to provide the optimum therapeutic response. For example, several divided doses can be administered or the dose can be proportionally reduced as indicated by the exigencies of the therapeutic situation. Booster administration may also be required.

The vaccine of the present invention can further comprise one or more additional immunomodulatory components such as, for example, an adjuvant or cytokine molecule, amongst others, that is capable of increasing the immune response against the immunogenic component. Non-limiting examples of adjuvants that can be used in the vaccine of the present invention include the RIBI adjuvant system (Ribi Inc., Hamilton, Mont., USA), alum, mineral gels such as aluminium hydroxide gel, oil-in-water emulsions, water-in-oil emulsions such as, for example, Block co-polymer (CytRx, Atlanta Ga., USA),QS-21 (Cambridge Biotech Inc., Cambridge Mass., USA), SAF-M (Chiron, Emeryville Calif., USA), AMPHIGEN® adjuvant, Freund's complete adjuvant; Freund's incomplete adjuvant; and Saponin, QuilA or other saponin fraction, monophosphoryl lipid A, and Avridine lipid-amine adjuvant. Other immunomodulatory agents that can be included in the vaccine include, for example, one or more cytokines, such as interferon and/or interleukin, or other known cytokines. Non-ionic surfactants such as, for example, polyoxyethylene oleyl ether and n-hexadecyl polyethylene ether may also be included in the vaccines of the present invention.

The vaccine composition can be administered in a convenient manner such as by oral, intravenous (where water soluble), intramuscular, subcutaneous, intranasal, intradermal or suppository routes or by implantation (e.g., using slow release technology). Depending on the route of administration, the immunogenic component may be required to be coated in a material to protect it from the action of enzymes, acids and other natural conditions which may inactivate it, such as those in the digestive tract.

The vaccine composition may also be administered parenterally or intraperitoneally. Dispersions can also be prepared in glycerol, liquid polyethylene glycols, and mixtures thereof, or in oils. Under ordinary conditions of storage and use, these preparations can contain a preservative to prevent the growth of microorganisms. Alternatively, the vaccine composition can be stored in lyophilised form to be rehydrated with an appropriate vehicle or carrier prior to use.

Pharmaceutical forms suitable for injectable use include sterile aqueous solutions (where water soluble) or dispersions and sterile powders for the extemporaneous preparation of sterile injectable solutions or dispersion. In all cases the form must be fluid to the extent that easy syringability exists, unless the pharmaceutical form is a solid or semi-solid such as when slow release technology is employed. In any event, it must be stable under the conditions of manufacture and storage and must be preserved against the contaminating action of microorganisms.

The carrier may be a solvent or dispersion medium containing, for example, water, ethanol, polyol (for example, glycerol, propylene glycol and liquid polyethylene glycol, and the like), suitable mixtures thereof and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents such as, for example, parabens, chlorobutanol, phenol, sorbic acid, thimerosal and the like. In many cases, it will be preferable to include isotonic agents such as, for example, sugars or sodium chloride. Prolonged absorption of the injectable compositions can be brought about by the use in the compositions of agents delaying absorption such as, for example, aluminum monostearate and gelatin.

Sterile injectable solutions are prepared by incorporating the active compound in the required amount in the appropriate solvent with various of the other ingredients enumerated above, as required, followed by filter-sterilization. Generally, dispersions are prepared by incorporating the sterilized active ingredient into a sterile vehicle which contains the basic dispersion medium and the required other ingredients selected from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The present invention extends to vaccine compositions which confer protection against infection by one or more isolates or sub-types of *L. intracellularis* including those that belong to the same serovar or serogroup as *Lawsonia intracellularis*. The vaccine composition preferably also confers protection against infection by other species of the genus *Lawsonia* or other microorganisms related thereto; as determined at the nucleotide, biochemical, structural, physiological and/or immunointeractive level; the only requirement being that said other species or other microorganism expresses a polypeptide which is immunologically cross-reactive to the polypeptide of the invention described herein. For example, such related microorganisms may comprise genomic DNA which is at least about 70% identical overall to the genomic DNA of *Lawsonia intracellularis* as determined using standard genomic DNA hybridisation and analysis techniques.

The terms "serogroup" and "serovar" relate to a classification of microorganisms which is based upon serological typing data, in particular data obtained using agglutination assays such as the microscopic agglutination test (MAT). Those skilled in the art will be aware that serovar and serogroup antigens are a mosaic on the cell surface and, as a consequence there will be no strict delineation between bacteria belonging to a serovar and/or serogroup. Moreover, organisms which belong to different species may be classified into the same serovar or serogroup because they are indistinguishable by antigenic determination. As used herein, the term "serovar" means one or more *Lawsonia* strains which are antigenically-identical with respect to antigenic determinants produced by one or more loci. Quantitatively, serovars may be differentiated from one another by cross-agglutination absorption techniques. As used herein, the term "serogroup" refers to a group of *Lawsonia* spp. whose members cross-agglutinate with shared group antigens and do not cross-agglutinate with the members of other groups and, as a consequence, the members of a serogroup have more or less close antigenic relations with one another by simple cross-agglutination.

The present invention thus clearly extends to vaccine compositions for the treatment and/or prophylaxis of animals, in particular, vaccine compositions for the treatment and/or prophylaxis of porcine and/or avian species, against any bacterium belonging to the same serovar or serogroup as *Lawsonia intracellularis*. Preferably, such organisms will express a polypeptide having an amino acid sequence identity of at least about 60% overall with respect to SEQ ID NO:1.

The present invention extends further to vaccine compositions capable of conferring protection against a "genetic variant" of *Lawsonia intracellularis*, the only requirement being that said variant expresses a polypeptide having an overall amino acid sequence identity of at least about 60% with respect to SEQ ID NO: 1 and/or comprises at least about 5 contiguous amino acid residues derived from SEQ ID NO:1 or a homologue, analogue or derivative thereof which is immunologically cross-reactive thereto. Genetic variants of *L. intracellularis* can be developed by mutation, recombination, conjugation or transformation of *L. intracellularis* or may occur naturally. It will be known to a person skilled in the art how to produce such derivatives.

In a particularly preferred embodiment, the vaccine composition of the invention is intended for or suitable for the prophylaxis and/or treatment of infection in a porcine or avian animal and more preferably, for prophylaxis and/or treatment of a porcine animal for infection by *L. intracellularis*.

Accordingly, the present invention clearly extends to the use of the immunogenic polypeptide of the invention according to any one of the preceding embodiments or as exemplified herein in the preparation of a medicament for the treatment and/or prophylaxis of PPE in animals, particularly porcine or avian animals.

The invention further extends to a method of treatment and/or prophylaxis of PPE in an animal such as an avian or porcine animal, said method comprising administering the vaccine composition or the immunogenic polypeptide of the invention as described or exemplified herein to said animal for a time and under conditions sufficient for an immune response to occur thereto. Preferably, in the case of administration of a vaccine composition, the immune response to the immunogen is a protective immune response.

Those skilled in the art will recognise the general applicability of the invention in vaccinating animals other than porcine and avian animals against *L. intracellularis* and/or related microorganisms. In the general application of the vaccine of the present invention, the only prerequisite is that the animal on which protection is conferred is capable of being infected with *Lawsonia intracellularis* and/or a related microorganism thereto and that, in the case of a related microorganism to *L. intracellularis*, said related microorganism expresses a B-cell or T-cell epitope which mimics or cross-reacts with the polypeptide component of the vaccine composition described herein. Animals which may be protected by the vaccine of the present invention include, but are not limited to, humans, primates, companion animals (e.g., cats, dogs), livestock animals (e.g., pigs, sheep, cattle, horses, donkeys, goats), laboratory test animals (e.g., mice, rats, guinea pigs, rabbits) and captive wild animals (e.g., kangaroos, foxes, deer). The present invention also extends to the vaccination of birds such as poultry birds, game birds and caged birds.

The present invention further extends to combination vaccines comprising an effective amount of a first immunogenic component comprising the polypeptide of the present invention combined with an effective amount of a second immunogenic component comprising one or more other antigens capable of protecting a porcine animal, or bird, against either *Lawsonia* spp. or another pathogen that infects and causes disease in said animal. In a preferred embodiment, the second immunogenic component is selected from the group consisting of the *L. intracellularis* autolysin, hemolysin, FlgE, and SodC polypeptides and homologues, analogues or derivatives thereof, in particular immunogenic variants or derivatives thereof, and nucleic acid molecules encoding same.

The isolated or recombinant OmpH polypeptide of the invention or an immunologically-equivalent homologue, analogue or derivative thereof is also useful for the preparation of immunologically interactive molecules which are useful in the diagnosis of infection of an animal by *Lawsonia* spp., in particular by *L. intracellularis* or a related organism thereto.

As used herein, the term "immunologically interactive molecule" includes antibodies and antibody derivatives and functional equivalents, such as a Fab, or a SCAB (single-chain antibody), any of which optionally can be conjugated to an enzyme, radioactive or fluorescent tag, amongst others. The only requirement of such immunologically interactive molecules is that they are capable of binding specifically to the immunogenic polypeptide of the present invention as hereinbefore described.

Accordingly, a further aspect of the invention extends to an immunologically interactive molecule which is capable of binding to any one or more of the following:
  (i) a peptide, oligopeptide or polypeptide which comprises an amino acid sequence which has at least about 60% sequence identity overall to the amino acid sequence set forth in SEQ ID NO: 1;
  (ii) a peptide comprising at least 5 contiguous amino acid residues derived from SEQ ID NO:1; or
  (iii) a homologue, analogue or derivative of (i) or (ii) which mimics a B-cell or T-cell epitope thereof.

In a preferred embodiment, the immunologically interactive molecule is an antibody that binds specifically to a polypeptide consisting of the amino acid of SEQ ID NO:1.

Conventional methods can be used to prepare the immunologically interactive molecules. For example, by using a polypeptide of the present invention, polyclonal antisera or monoclonal antibodies can be made using standard methods. For example, a mammal, (e.g., a mouse, hamster, or rabbit) can be immunized with an immunogenic form of the polypeptide of the present invention which elicits an antibody response in the mammal. Techniques for conferring immunogenicity on a polypeptide include conjugation to carriers, or other techniques well known in the art. For example, the polypeptide can be administered in the presence of adjuvant or can be coupled to a carrier molecule, as known in the art, that enhances the immunogenicity of the polypeptide. The progress of immunization can be monitored by detection of antibody titres in plasma or serum. Standard ELISA or other immunoassay can be used with the immunogen as antigen to assess the levels of antibodies. Following immunization, antisera can be obtained and, for example, IgG molecules corresponding to the polyclonal antibodies can be isolated from the antisera.

To produce monoclonal antibodies, antibody producing cells (lymphocytes) can be harvested from an animal immunised with a peptide of the present invention and fused with myeloma cells by standard somatic cell fusion procedures, thus immortalizing these cells and yielding hybridoma cells. Such techniques are well known in the art, and include, for example, the hybridoma technique originally developed by Kohler and Milstein (1975), as well as other techniques such as the human B-cell hybridoma technique (Kozbor et al., 1983), the EBV-hybridoma technique to produce human monoclonal antibodies (Cole et al., 1985), and screening of combinatorial antibody libraries (Huse et al., 1989). Hybridoma cells can be isolated and screened immunochemically for production of antibodies that are specifically reactive with the polypeptide and monoclonal antibodies isolated therefrom.

As with all immunogenic compositions for eliciting antibodies, the immunogenically effective amounts of the peptides of the invention must be determined empirically. Factors to be considered include the immunogenicity of the native peptide, whether or not the peptide will be complexed with or covalently attached to an adjuvant or carrier protein or other carrier, the route of administration for the composition, i.e., intravenous, intramuscular, subcutaneous, etc., and the number of immunizing doses to be administered. Such factors are known in the vaccine art and it is well within the skill of immunologists to make such determinations without undue experimentation.

The term "antibody" as used herein, is intended to include fragments thereof which are also specifically reactive with a peptide that mimics or cross-reacts with a B-cell or T-cell epitope of the *Lawsonia intracellularis* OmpH polypeptide set forth in SEQ ID NO: 1. Antibodies can be fragmented using conventional techniques and the fragments screened for utility in the same manner as described above for whole antibodies. For example, F(ab')2 fragments can be generated by treating antibody with pepsin. The resulting F(ab')2 fragment can be treated to reduce disulfide bridges to produce Fab' fragments.

It is within the scope of this invention to include any secondary antibodies (monoclonal, polyclonal or fragments of antibodies), including anti-idiotypic antibodies, directed to the first mentioned antibodies discussed above. Both the first and second antibodies can be used in detection assays or a first antibody can be used with a commercially available anti-immunoglobulin antibody. An antibody as contemplated herein includes any antibody specific to any region of a peptide which mimics, or cross-reacts with a B-cell or T-cell epitope of the *Lawsonia intracellularis* OmpH polypeptide set forth in SEQ ID NO:1 as hereinbefore described.

The antibodies described herein are useful for determining B-cell or T-cell epitopes of the amino acid sequence set forth in SEQ ID NO: 1 such as, for example, by testing the ability of synthetic peptides to cross-react immunologically with said amino acid sequence or to elicit the production of antibodies which cross-react with said amino acid sequence. Using methods described herein, polyclonal antibodies, monoclonal antibodies or chimeric monoclonal antibodies can also be raised to peptides which mimic or cross-react with a B-cell or T-cell epitope of the *Lawsonia intracellularis* OmpH polypeptide set forth in SEQ ID NO:1.

More particularly, the polyclonal, monoclonal or chimeric monoclonal antibodies can be used to detect the peptides of the invention and/or any homologues, analogues or derivatives thereof, in various biological materials. For example, they can be used in an ELISA, radioimmunoassay, or histochemical test. In other words, the antibodies can be used to test for binding to a polypeptide of the invention or to a homologue, analogue or derivative thereof, in a biological sample to diagnose the presence of *Lawsonia intracellularis* therein.

Accordingly, a further aspect of the invention provides a method of diagnosing infection of an animal by *Lawsonia intracellularis* or a related microorganism thereto, said method comprising the steps of contacting a biological sample derived from said animal with an immunologically interactive molecule which is capable of binding to a peptide, oligopeptide or polypeptide comprising the amino acid sequence set forth in SEQ ID NO:1 or a homologue, analogue or derivative thereof, for a time and under conditions sufficient for an antigen:antibody complex to form, and then detecting said complex formation. According to this embodiment of the present invention, the immunologically interactive molecule is preferably an antibody molecule prepared against the *Lawsonia intracellularis* OmpH polypeptide set forth in SEQ ID NO:1 or an analogue or derivative thereof.

The biological sample is one which might contain a polypeptide having an amino acid sequence set forth in SEQ ID NO:1 or a homologue, analogue or derivative thereof, in particular a biological sample derived from a porcine or avian host of the pathogen *Lawsonia intracellularis* or a related microorganism thereto, and can include any appropriate tissue or fluid sample from the animal. Preferred biological samples are derived from the ileum, caecum, small intestine, large intestine, whole serum or lymph nodes of the porcine or avian host animal being tested. Alternatively or in addition the biological test sample may comprise faeces or a rectal swab derived from the animal.

To distinguish *L. intracellularis* from other microorganisms resident in the gut or other organ of an animal, the antibodies should not be prepared against highly-conserved epitopes of OmpH such as those regions of at least 5 amino acids in length which are conserved between *L. intracellularis* and a microorganism which is present in the gut or other organ of an animal in respect of which diagnosis is sought, for example *E. coli*.

Conventional immunoassays can be used to perform this embodiment of the invention. A wide range of immunoassay techniques are available as can be seen by reference to U.S. Pat. Nos. 4,016,043, 4,424,279 and 4,018,653. These, of course, include both single-site and two-site or "sandwich" assays of the non-competitive types, as well as the traditional competitive binding assays. These assays also include direct binding of a labelled antibody to a target. It will be readily apparent to the skilled technician how to modify or optimise such assays to perform this embodiment of the present invention, and all such modifications and optimisations are encompassed by the present invention.

In one alternative embodiment, the present invention contemplates a method of identifying whether or not an animal has suffered from a past infection, or is currently infected with *Lawsonia intracellularis* or a related microorganism thereto, said method comprising contacting blood or serum derived from said animal with the immunogenic polypeptide of the invention for a time and under conditions sufficient for an antigen:antibody complex to form, and detecting said complex formation. This embodiment differs from the embodiment described supra in that it relies upon the detection of circulating antibodies against *Lawsonia intracellularis* or related organism in the animals blood or serum which are present as a consequence of a past or present infection by this pathogen. However, it will be apparent to those skilled in the art that the principle of the assay format is the same. As with other embodiments of the invention referred to supra, conventional immunoassays can be used. Persons skilled in the art will readily be capable of varying known immunoassay formats to perform the present embodiment. This embodiment of the invention can also utilise derivatives of blood and serum which comprise immunologically interactive molecules such as, for example, partially-purified IgG or IgM fractions and buffy coat samples, amongst others. The preparation of such fractions will also be known to those skilled in the art.

A further aspect of the present invention provides an isolated nucleic acid molecule which comprises a sequence of nucleotides which encodes, or is complementary to a nucleic acid molecule which encodes, a peptide, oligopeptide or polypeptide selected from the following:

(i) a peptide, oligopeptide or polypeptide which comprises an amino acid sequence having at least about 60% sequence identity overall to the amino acid sequence set forth in SEQ ID NO:1;

(ii) a peptide comprising at least 5 contiguous amino acids derived from SEQ ID NO:1; or (iii) a homologue, analogue or derivative of (i) or (ii) which mimics a B-cell or T-cell epitope of *Lawsonia* spp.

In a preferred embodiment, the present invention provides an isolated nucleic acid molecule comprising a sequence of nucleotides which encodes, or is complementary to a nucleic acid molecule which encodes, a polypeptide immunogen which comprises, mimics or cross-reacts with a B-cell or T-cell epitope of the *Lawsonia intracellularis* OmpH polypeptide set forth in SEQ ID NO:1.

In a particularly preferred embodiment, the present invention provides an isolated nucleic acid molecule comprising a sequence of nucleotides encoding the *L. intracellularis* OmpH polypeptide having an amino acid sequence set forth in SEQ ID NO: 1.

It is within the scope of the invention to encompass polymeric forms of the immunogenic polypeptide described herein, such as aggregates of the amino acid sequence set forth in SEQ ID NO:1 or a homologue, analogue or derivative thereof or, alternatively, as polypeptides comprising repeats of the amino acid sequence set forth in SEQ ID NO: 1 or a homologue, analogue or derivative thereof. The present invention extends further to nucleic acid molecules encoding such polymeric forms. thereof.

Alternatively or in addition, the isolated nucleic acid molecule of the invention further comprises a sequence of nucleotides which has at least about 60% overall sequence identity to the nucleotide sequence set forth in SEQ ID NO:2 or to a complementary nucleotide sequence thereof. More preferably, the percentage sequence identity to SEQ ID NO:2 or to a complementary nucleotide sequence thereto is at least about 80%. Still more preferably, the percentage sequence identity is at least about 90%. Yet still more preferably, the percentage sequence identity is at least about 95%.

In a preferred embodiment, the nucleic acid molecule comprises the nucleotide sequence set forth in SEQ ID NO:2, or the OmpH-encoding nucleotide sequence present in pALK13 (ATCC 207196), or a degenerate variant thereof, and complements thereof.

In determining whether or not two nucleotide sequences fall within these percentage limits, those skilled in the art will be aware that it is necessary to conduct a side-by-side comparison or multiple alignment of sequences. In such comparisons or alignments, differences may arise in the positioning of non-identical residues, depending upon the algorithm used to perform the alignment. In the present context, reference to a percentage identity between two or more nucleotide sequences shall be taken to refer to the number of identical residues between said sequences as determined using any standard algorithm known to those skilled in the art. For example, nucleotide sequences may be aligned and their identity calculated using the BESTFIT programme or other appropriate programme of the Computer Genetics Group, Inc., University Research Park, Madison, Wis., United States of America (Devereaux et al, 1984).

Alternatively or in addition, the isolated nucleic acid molecule of the invention is further capable of hybridising under at least low stringency conditions to the nucleotide sequence set forth in SEQ ID NO:2 or a complementary nucleotide sequence thereto or a nucleic acid fragment comprising at least about 20 contiguous nucleotides in length derived from the sequence set forth in SEQ ID NO:2 or a complementary nucleotide sequence thereto.

Preferably, said nucleic acid molecule is capable of hybridising under at least moderate stringency conditions, and even more preferably under high stringency conditions.

The present invention clearly encompasses genetic constructs comprising the subject nucleic acid molecule in an expressible format suitable for the preparation of a recombinant immunogenic polypeptide of the present invention, such as for use in recombinant univalent or polyvalent recombinant vaccines.

In such cases, the nucleic acid molecule will be operably connected to a promoter sequence, which can thereby regulate expression of said nucleic acid molecule in a prokaryotic or eukaryotic cell as described supra.

The genetic construct optionally further comprises a terminator sequence. The term "terminator" refers to a DNA sequence at the end of a transcriptional unit which signals termination of transcription. A "terminator" is a nucleotide sequence, generally located within the 3'-non-translated region of a gene or mRNA, comprising a polyadenylation signal to facilitate the post-transcriptional addition of a polyadenylate sequence to the 3'-end of a primary mRNA transcript. Terminator sequences may be isolated from the genetic sequences of bacteria, fungi, viruses, animals and/or plants. Terminators active in animal cells are known and described in the literature.

In a preferred embodiment, the genetic construct can be a cloning or expression vector, as known in the art, such as a plasmid, cosmid, or phage, comprising a nucleic acid molecule of the present invention, and host cells transformed or transfected therewith. In a non-limiting embodiment, the vector is plasmid pALK13 (ATCC Accession No. 207196).

The genetic constructs of the present invention are particularly useful for producing the proteinaceous immunogenic component of the vaccine composition described herein or for use in a DNA vaccine.

A range of genetic diagnostic assays to detect infection of an animal by Lawsonia intracellularis or a related microorganism can be employed using the nucleic acid molecule described herein such as, for example, assays based upon the polymerase chain reaction (PCR) and nucleic acid hybridisation. All such assays are contemplated in the present invention.

Accordingly, a still further aspect of the invention provides a diagnostic method of detecting Lawsonia intracellularis or related microorganism in a biological sample derived from an animal subject, said method comprising the steps of hybridising one or more probes or primers derived from the nucleotide sequence set forth in SEQ ID NO:2 or a complementary nucleotide sequence thereto or a homologue, analogue or derivative thereof, to a DNA or RNA molecule present in said sample and then detecting said hybridisation using a detection means.

As used herein, the term "probe" refers to a nucleic acid molecule which is derived from the nucleotide sequence set forth in SEQ ID NO:2 and which is capable of being used in the detection thereof. Probes may comprise DNA (single-stranded or double-stranded) or RNA (i.e., riboprobes) or analogues thereof.

The term "primer" refers to a probe as hereinbefore defined which is further capable of being used to amplify a nucleotide sequence from Lawsonia intracellularis or a related microorganism thereto in a PCR.

Preferred probes and primers include fragments of the nucleotide sequence set forth in SEQ ID NO:2 and synthetic single-stranded DNA or RNA molecules of at least about 15 nucleotides in length derived from the sequence set forth in SEQ ID NO:2 or a complementary nucleotide sequence thereto.

Preferably, probes and primers according to this embodiment will comprise at least about 20 contiguous nucleotides derived from SEQ ID NO:2 or a complementary sequence thereto, even more preferably at least about 25 contiguous nucleotides, still even more preferably at least about 50 contiguous nucleotides and even more preferably at least about 100 nucleotides to about 500 nucleotides derived from the sequence set forth in SEQ ID NO:2 or a complement thereof. Probes and primers comprising the full-length of SEQ ID NO:2 or a complementary nucleotide sequence thereto are also encompassed by the present invention.

For the present purpose, "homologues" of a nucleotide sequence shall be taken to refer to an isolated nucleic acid molecule which encodes a polypeptide that is functionally equivalent to the polypeptide encoded by the nucleic acid molecule of the present invention or to a polypeptide which is a homologue, analogue or derivative of SEQ ID NO: 1, notwithstanding the occurrence within said sequence, of one or more nucleotide substitutions, insertions, deletions, or rearrangements.

"Analogues" of a nucleotide sequence set forth herein shall be taken to refer to an isolated nucleic acid molecule which encodes a functionally-equivalent polypeptide to the polypeptide encoded by the nucleic acid molecule of the present invention or a homologue, analogue or derivative of a polypeptide having the amino acid sequence of SEQ ID NO:1, notwithstanding the occurrence of any non-nucleotide constituents not normally present in said isolated nucleic acid molecule such as, for example, carbohydrates, radiochemicals including radio nucleotides, reporter molecules such as, but not limited to biotin, DIG, alkaline phosphatase or horseradish peroxidase, amongst others.

"Derivatives" of a nucleotide sequence set forth herein shall be taken to refer to any isolated nucleic acid molecule which contains at least about 50% nucleotide sequence identity to 15 or more contiguous nucleotides present in the nucleotide sequence set forth in SEQ ID NO:2 or a complementary nucleotide sequence thereto. Generally, the nucleotide sequence of the present invention may be subjected to mutagenesis to produce single or multiple nucleotide substitutions, deletions and/or insertions. Nucleotide insertional derivatives of the nucleotide sequence of the present invention include 5' and 3' terminal fusions as well as intra-sequence insertions of single or multiple nucleotides or nucleotide analogues. Insertional nucleotide sequence variants are those in which one or more nucleotides or nucleotide analogues are introduced into a predetermined site in the nucleotide sequence of said sequence, although random insertion is also possible with suitable screening of the resulting product being performed. Deletional nucleotide sequence variants are characterised by the removal of one or more nucleotides from the nucleotide sequence. Substitutional nucleotide sequence variants are those in which at least one nucleotide in the sequence has been removed and a different nucleotide or nucleotide analogue inserted in its place. In a preferred embodiment, such substitutions are selected based on the degeneracy of the genetic code, as known in the art, with the resulting substitutional variant encoding the amino acid sequence of SEQ ID NO:1.

Probes or primers can comprise inosine, adenine, guanine, thymidine, cytidine or uracil residues or functional analogues or derivatives thereof that are capable of being incorporated into a polynucleotide molecule, provided that the resulting probe or primer is capable of hybridising under at least low stringency conditions to SEQ ID NO:2 or to a complementary nucleotide sequence thereof, or is at least about 60% identical to SEQ ID NO:2 or to a complementary nucleotide sequence thereof.

The biological sample according to this aspect of the invention includes any organ, tissue, cell or exudate which contains or is likely to contain *Lawsonia intracellularis* or a nucleic acid derived therefrom. A biological sample can be prepared in a suitable solution such as, for example, an extraction buffer or suspension buffer. The present invention extends to the testing of biological solutions thus prepared, the only requirement being that said solution at least comprises a biological sample as described herein.

The diagnostic assay of the present invention is useful for the detection of *Lawsonia intracellularis* or a microorganism which is related thereto which expresses the OmpH polypeptide of the present invention or a OmpH-like polypeptide.

The present invention clearly contemplates diagnostic assays which are capable of both genus-specific and species-specific detection. Accordingly, in one embodiment, the probe or primer, or a homologue, analogue or derivative thereof, comprises DNA capable of being used to detect multiple *Lawsonia* spp. In an alternative embodiment, the probe or primer or a homologue, analogue or derivative thereof comprises DNA capable of being used to distinguish *Lawsonia intracellularis* from related microorganisms.

Less-highly conserved regions within SEQ ID NO:2, are particularly useful as species-specific probes and/or primers for the detection of *L. intracellularis* and very closely related species.

Furthermore, the diagnostic assays described herein can be adapted to a genus—specific or species-specific assay by varying the stringency of the hybridisation step. Accordingly, a low stringency hybridisation can be used to detect several different species of *Lawsonia* in one or more biological samples being assayed, while a high stringency hybridisation can be used to distinguish *Lawsonia intracellularis* from such other species.

The detection means according to this aspect of the invention may be any nucleic acid-based detection means such as, for example, nucleic acid hybridisation techniques or paper chromatography hybridisation assay (PACHA), or an amplification reaction such as PCR, or nucleic acid sequence-based amplification (NASBA) system. The invention further encompasses the use of different assay formats of said nucleic acid-based detection means, including restriction fragment length polymorphism (RFLP), amplified fragment length polymorphism (AFLP), single-strand chain polymorphism (SSCP), amplification and mismatch detection (AMD), interspersed repetitive sequence polymerase chain reaction (IRS-PCR), inverse polymerase chain reaction (iPCR), in situ polymerase chain reaction and reverse transcription polymerase chain reaction (RT-PCR), amongst others.

Where the detection means is a nucleic acid hybridisation technique, the probe can be labelled with a reporter molecule capable of producing an identifiable signal (e.g., a radioisotope such as $^{32}P$ or $^{35}S$, or a biotinylated molecule). According to this embodiment, those skilled in the art will be aware that the detection of said reporter molecule provides for identification of the probe and that, following the hybridisation reaction, the detection of the corresponding nucleotide sequences in the biological sample is facilitated. Additional probes can be used to confirm the assay results obtained using a single probe.

A variation of the nucleic acid hybridisation technique contemplated by the present invention is the paper chromatography hybridisation assay (PACHA) described by Reinhartz et al. (1993) and equivalents thereof, wherein a target nucleic acid molecule is labelled with a reporter molecule such as biotin, applied to one end of a nitrocellulose or nylon membrane filter strip and subjected to chromatography under the action of capillary or other forces (e.g., an electric field) for a time and under conditions sufficient to promote migration of said target nucleic acid along the length of said membrane to a zone at which a DNA probe is immobilised thereto, for example, in the middle region. According to this detection format, labelled target nucleic acid comprising the *Lawsonia* spp. nucleotide sequences complementary to the probe will hybridise thereto and become immobilised in that region of the membrane to which the probe is bound. Non-complementary sequences to the probe will diffuse past the site at which the probe is bound. The target nucleic acid may comprise a crude or partially-pure extract of DNA or RNA or, alternatively, an amplified or purified DNA. Additional variations of this detection means which utilise the nucleotide sequences described herein are clearly encompassed by the present invention.

Wherein the detection means is a RFLP, nucleic acid derived from the biological sample, in particular DNA, is digested with one or more restriction endonuclease enzymes and the digested DNA is subjected to electrophoresis, transferred to a solid support such as, for example, a nylon or nitrocellulose membrane, and hybridised to a probe optionally labelled with a reporter molecule, as hereinbefore defined. According to this embodiment, a specific pattern of DNA fragments is displayed on the support, wherein said pattern is preferably specific for a particular *Lawsonia* species to enable the user to distinguish between different species of the bacterium.

Wherein the detection means is an amplification reaction such as, for example, a polymerase chain reaction or a nucleic acid sequence-based amplification (NASBA) system or a variant thereof, one or more nucleic acid primer molecules of at least 15 contiguous nucleotides in length derivable from SEQ ID NO:2 or its complementary nucleotide sequence, or a homologue, analogue or derivative thereof, is hybridised to nucleic acid derived from a biological sample, and nucleic acid copies of the OmpH-encoding genetic sequences in said sample, or a part or fragment thereof, are enzymically-amplified.

Those skilled in the art will be aware that there must be a sufficiently high percentage of nucleotide sequence identity between the primers and the sequences in the biological sample template molecule to which they hybridise (i.e., the "template molecule"). As stated previously, the stringency conditions can be selected to promote hybridisation.

Preferably, each primer is at least about 95% identical to a region of SEQ ID NO:2 or its complementary nucleotide sequence in the template molecule to which it hybridises. Those skilled in the art will also be aware that, in one format, PCR provides for the hybridisation of non-complementary primers to different strands of the template molecule, such that the hybridised primers are positioned to facilitate the 5'–3' synthesis of nucleic acid in the intervening region, under the control of a thermostable DNA polymerase enzyme. As a consequence, PCR provides an advantage over other detection means in so far as the nucleotide sequence in the region between the hybridised primers may be unknown and unrelated to any known nucleotide sequence.

In an alternative embodiment, wherein the detection means is AFLP, the primers are selected such that, when nucleic acid derived from the biological sample, in particular DNA, is amplified, different length amplification products are produced from different *Lawsonia* spp. The amplification products can be subjected to electrophoresis, transferred to a solid support such as, for example, a nylon or nitrocellulose membrane, and hybridised to a probe optionally labelled with a reporter molecule, as hereinbefore described. According to this embodiment, a specific pattern of amplified DNA fragments is displayed on the support, said pattern optionally specific for a particular *Lawsonia* ssp., to enable the user to distinguish between different species of the bacterium in much the same way as for RFLP analysis.

The technique of AMD facilitates, not only the detection of *Lawsonia* spp. DNA in a biological sample, but also the determination of nucleotide sequence variants which differ from the primers and probes used in the assay format. Wherein the detection means is AMD, the probe is end-labelled with a suitable reporter molecule and mixed with an excess of the amplified template molecule. The mixtures are subsequently denatured and allowed to renature to form nucleic acid "probe:template hybrid molecules" or "hybrids", such that any nucleotide sequence variation between the probe and the temple molecule to which it is hybridised will disrupt base-pairing in the hybrids. These regions of mismatch are sensitive to specific chemical modification using hydroxylamine (mismatched cytosine residues) or osmium tetroxide (mismatched thymidine residues), allowing subsequent cleavage of the modified site using piperidine. The cleaved nucleic acid may be analysed using denaturing polyacrylamide gel electrophoresis, followed by standard nucleic acid hybridisation as described supra, to detect the *Lawsonia*-derived nucleotide sequences. Those skilled in the art will be aware of the means of end-labelling a genetic probe according to the performance of the invention described in this embodiment.

According to this embodiment, the use of a single end-labelled probe allows unequivocal localisation of the sequence variation. The distance between the point(s) of sequence variation and the end-label is represented by the size of the cleavage product.

In an alternative embodiment of AMD, the probe is labelled at both ends with a reporter molecule, to facilitate the simultaneous analysis of both DNA strands.

Wherein the detection means is RT-PCR, the nucleic acid sample comprises an RNA molecule which is a transcription product of *Lawsonia*-derived DNA or a homologue, analogue or derivative thereof. As a consequence, this assay format is particularly useful when it is desirable to determine expression of one or more *Lawsonia* genes. According to this embodiment, the RNA sample is reverse-transcribed to produce the complementary single-stranded DNA which is subsequently amplified using standard procedures.

Variations of the embodiments described herein are described in detail by McPherson et al. (1991).

The present invention clearly extends to the use of any and all detection means referred to supra for the purposes of diagnosing *Lawsonia* spp. and in particular *Lawsonia intracellularis* infection in animal.

The amplification reaction detection means described supra can be further coupled to a classical hybridisation reaction detection means to further enhance sensitivity and specificity of the inventive method, such as by hybridising the amplified DNA with a probe which is different from any of the primers used in the amplification reaction. Similarly, the hybridisation reaction detection means described supra can be further coupled to a second hybridisation step employing a probe which is different from the probe used in the first hybridisation reaction.

A further aspect of the invention provides an isolated probe or primer derived from SEQ ID NO:2 or a complementary nucleotide sequence thereto.

The present invention is further described by the following non-limiting examples.

EXAMPLE 1

Sources of Pig Tissue

Infected Pig Intestines

Sections of grossly thickened ilea were taken from pigs naturally or experimentally affected by PPE. The presence of *L. intracellularis* bacteria in the ilea was confirmed using immunofluorescent staining with specific monoclonal antibodies (McOrist et al, 1987). An example of a suitable antibody is monoclonal antibody IG4 available from the University of Edinburgh, UK.

EXAMPLE 2

Isolation of *Lawsonia Intracellularis* Bacteria from the Infected Pig Ileum

*Lawsonia intracellularis* bacteria were extracted directly from lesions of PPE in pigs by filtration and further purified over a Percoll (Pharmacia, Uppsala, Sweden) gradient as follows. Infected ilea were collected from pigs and the presence of *L. intracellularis* was confirmed histologically before storage at −80° C. Sections of ileum were thawed and approximately 8 g of infected mucosa were scraped from the intestinal wall. The mucosa was homogenised with 40 ml sterile phosphate buffered saline (PBS) on half speed for 10 seconds using a Sorvall omnimixer. This suspension was centrifuged at 2000×g for 4 minutes. The supernatant was discarded and the cell pellet was resuspended in 40 ml PBS and re-centrifuged. This washing step was repeated twice. The cell pellet was then resuspended in 20 ml PBS and homogenised at full speed for one minute to release *L. intracellularis* bacteria.

This homogenate was centrifuged at 1000×g for 4 minutes giving a pellet containing a crude mixture of homogenised epithelial cells and intestinal bacteria. The supernatant was filtered using filters with pore sized 3 µm, 1.2 µm and 0.8 µm (Millipore Corporation, MA, USA). The filtrate was centrifuged at 8000×g for 30 minutes, resulting in a small pellet of *L. intracellularis* bacteria. The *L. intracellularis* bacteria were further purified using a 45% self forming Percoll gradient as follows: 2 ml of the bacterial preparation was mixed by inversion into 30 ml of a 45% self forming Percoll (Pharmacia LKB, Uppsala, Sweden) gradient (45% v/v of Percoll, 150 mM NaCl). The gradients were centrifuged in a Sorval centrifuge using the SS34 rotor, at 20,000 rpm for 30 minutes at 4° C. Usually a number of bands form within the gradient. The band (usually located approx. 10–20 mm from the base of the tube) containing the L. intracellularis bacteria was collected and the volume made up to 16 ml with PBS. The solution was then centrifuged for 15 minutes at 8000 rpm. The resultant pellet was washed with PBS before being resuspended in a final volume of approximately one ml.

EXAMPLE 3

Purification of Lawsonia Intracellularis Genomic DNA

Genomic DNA was extracted from Percoll-gradient purified Lawsonia intracellularis bacteria recovered from infected pig ilea scrapings (Example 2) by the methods described by Anderson et al (1984) and Sambrook et al (1989).

Briefly, the L. intracellularis cells were pelleted by centrifugation at 14,000×g at 4° C. for 15 min. The cells were resuspended in 10 ml of TE buffer (1 mM Tris-HCl, 0.1 mM EDTA, pH 8.0) and centrifuged as before. The pellet was then resuspended in 4 ml of TE buffer containing 4 mg/ml lysozyme (Sigma Chemical Co.) and incubated at 37° C. for 20 min. SDS and proteinase K (Promega, Wis., USA) were added to final concentrations of 1% (w/v) and 200 µg/ml, respectively, and incubation was continued at 45° C. for 4 hours. The lysate was then extracted with an equal volume of phenol, phenol:chloroform (1:1) and chloroform, respectively, and the nucleic acids were recovered from the supernatant by ethanol precipitation. The pellet was gently dissolved in TE, treated with RnaseA (Promega, Wis., USA) at 37° C. for 30 min and then digested with proteinase K in the presence of 0.5% (w/v) SDS for 1 h at 50° C. After another round of phenol:chloroform (1:1) and ethanol precipitation, the purified DNA was dissolved in TE. The DNA was then stored at 4° C.

EXAMPLE 4

Immunoscreening of A L. Intracellularis Library Using Experimental Sera from Vaccinated Pigs The genomic DNA from Example 3 was partially digested with the restriction endonuclease Sau3A (Promega) and ligated into Lambda ZAP Express (Stratagene, Calif., USA). The lambda library was plated on a lawn of E. coli XLI-Blue cells at a density of 1,000 phage forming units (pfu) per 150 mm L-broth agar plate. The library was screened using the method described in the Protoblot Technical Manual (Promega, Wis., USA). The filters were blocked in blocking buffer (10 mM Tris-HCl, pH 8.0, 150 mM NaCl, 0.05% Tween 20 and 5% blotto,) prior to screening with sera from the pigs Y12 and/or 395. The pigs Y12 and 395 had previously been immunised with formalin-killed L. intracellularis and heat-killed L. intracellularis, respectively, as described in International Patent Application No. PCT/AU96/00767. Positive plaques identified in the primary screen were picked, replated at a lower density and rescreened with either or both sera until an individual positive plaque was identified. Plasmid DNA from the positive lambda phage clone was isolated by in vivo excision, as recommended by the manufacturer (Stratagene, Calif., USA).

EXAMPLE 5

Analysis of L. Intracellularis Expressing Phage Clones

Phagemid DNA from positive λZAP Express phage clones was isolated by in vivo excision, by the conditions recommended by the manufacturer (Stratagene).

Plasmid DNA for restriction analysis was extracted by alkaline-lysis, as described by Sambrook et al (1989), and for automated sequencing, using the High Pure Plasmid Kit, as recommended by the manufacturer (Boehringer Mannheim, Mannheim, Germany). DNA sequencing of isolated clone inserts was performed by the Dye-terminator method of automated sequencing (ABI Biosystems, CA, USA). The nucleotide sequence of the complete coding region of the OmpH gene is set out in SEQ ID NO: 2.

EXAMPLE 6

Western Analysis of E. Coli Clones Expressing L. Intracellularis OmpH Protein

An overnight culture was diluted 1/10 in 10 ml LB broth containing appropriate antibiotic selection. After incubation at 37° C. on an orbital shaker for 30 min, a final concentration of 1 mM IPTG was added and the cultures incubated for a further 1–2 hours. Cells (1.5 ml) were harvested by centrifugation, resuspended in 50 µl of sample buffer (62.4 mM HCl, 2% w/v SDS, 10% glycerol, 5% v/v mercaptoethanol, 0.002% bromophenol blue, pH 6.8) and heated to 95° C. for 5 min before separating solubilised proteins electrophoretically on a 12% protein gel at 200V for 2 hours.

Proteins were transferred to a nitrocellulose membrane using the standard procedure, as recommended by the manufacturer (BioRad, CA). The membrane was blocked and screened with Y12 sera, as described in Example 4. Enhanced chemiluminescence (ECL, Amersham, Ill.) was used to detect the immunoreactive L. intracellularis protein. Data are presented in FIG. 1.

EXAMPLE 7

Antisera to L. Intracellularis recOmpH protein

Antisera to purified recombinant L. intracellularis OmpH protein were raised in rabbits. Rabbits were injected intramuscularly at two separate sites with a preparation of purified recombinant OmpH protein. A total of 400 µg of purified OmpH was formulated with Freund's incomplete adjuvant to make a total volume of 1 ml, and 500 µl was injected at each site. Similarly, another two doses were prepared for a second vaccination 28 days later, injected subcutaneously. Two weeks later the rabbit was euthanised and blood samples were collected.

EXAMPLE 8

Fluorescent Antibody Stain Using Rabbit Anti OmpH for Paraffin Sections and Faecal Smears Formalin fixed paraffin sections were cut onto poly-L-lysine coated slides and dried at 60° C. and then rehydrated. They were then digested in 0.1% trypsin, twice, for 5 min each at 37° C. Faecal smears were taken using a cotton tipped swab which was then smeared onto a glass slide. The slide was then air dried before being fixed in acetone for 10 min.

Figure 2:
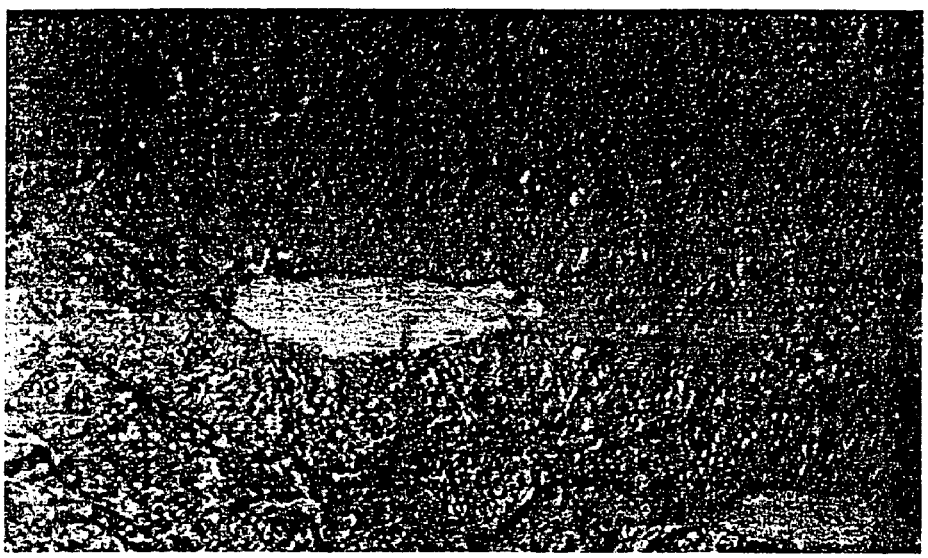
FIG. 2A is a copy of a phase contrast micrograph of a cross-section or porcine ileum tissue that has been infected with *Lawsonia intracellularis*. The central oval feature represents the lumen surrounded by immature mucosal cells.
FIG. 2B is a copy of a fluorescence micrograph of a cross-section of porcine ileum tissue that has been infected with *Lawsonia intracellularis* showing the localisation of OmpH using anti-OmpH serum and detection using FITC following excitation with ultraviolet light. Fluorescence is localised to *L. intracellularis* within the apical cytoplasm of the mucosal cells. There is no detectable binding of the primary antibody to other material in the section.
Figure 2:

Slides were washed twice in PBST for 7 min. Following the application of a coverslip, the slides were incubated in rabbit anti-OmpH antiserum (see previous example), diluted in PBS to 1:50, at room temperature for 1 hour. The coverslip was removed and the slides were washed (PBST for 7 min, ×3) before the addition of 30 µl of a 1/75 dilution of the FITC conjugated anti-rabbit antiserum (Sigma, MO) and a coverslip. The slides were incubated at room temperature for a further 1 hr. The coverslip was removed and the slides were washed with PBST, as before, with a final additional rinse in PBS. The slides were then mounted using 9 parts glycerol: 1 part PBS solution and a glass cover slip applied. The fluorescent bacteria were visualised under high power (×1200) at 340 nm using a Lietz laborlux S microscope. Data are presented in FIGS. 2A and 2B.

EXAMPLE 9

Identification of L. Intracellularis Components

Sequence similarity of the DNA molecules encoding putative vaccine candidates identified from Example 4 and 5, was identified using the Clustal W algorithm (Thompson et al., 1994). The aligned amino acid sequences of putative L. intracellularis OmpH (SEQ ID NO:1), Yersinia enterolytica OmpH and Yersinia pseudotuberculosis OmpH polypeptides share approximately 20% amino acid sequence identity and approximately 35% amino acid similarity overall. Additionally, the aligned amino acid sequences of putative L. intracellularis OmpH (SEQ ID NO:1), Yersinia enterolytica OmpH, Yersinia pseudotuberculosis OmpH and Haemophilua influenzae OmpH polypeptides share only approximately 12% amino acid sequence identity and approximately 25% amino acid similarity overall. (FIG. 3). Unique regions of the Lawsonia intracellularis OmpH polypeptide are apparent from a comparison of the amino acid sequence of this polypeptide to those from other microorganisms (FIG. 3).

EXAMPLE 10

Preparation of Biological Material for Deposit—Amplification of ompH

Template DNA for ompH was plasmid pCLO1. Plasmid pCLO1 was excised from Lambda ZAPII (Stratagene Cloning Systems, La Jolla, Calif.) and is a pBluescript SK-derivative, which was identified by screening a L. intracellularis genomic lambda library with α-L. intracellularis antisera.

The PCR amplifications consisted of 0.1 ng of plasmid template, 1 µM each of forward (RA176: 5'TTTATTCAT-TCAGAAGGAGCTTC 3'; SEQ ID NO:3) and reverse primers (RA177: 5' AAGTTTAGCAATTTCTGAAAG 3'; SEQ ID NO:4), 7.5 units KlenTaql polymerase (Ab Peptides, Inc., St. Louis, Mo.), 0.075 units Pfu polymerase (Stratagene Cloning Systems, La Jolla, Calif.) 1×PC2 (Klen-Taql) buffer and 0.2 mM dNTPs in a 50 µl volume. PCR was carried out in 4 stages: (i) 95° C. for 5 min (5'); (ii) 94° C. for 1 min, 58° C. for 30 seconds, 72° C. for 1.5 min, ×33 cycles; (iii) 72° C. for min, (iv) hold at 4° C.

The PCR fragment encoding the ompH gene of L. intracellularis was subcloned into pCR2.1-TOPO (Invitrogen Corp., Carlsbad, Calif.) and designated pALK13.

Microorganism Deposits

The plasmid pALK13 was deposited with the American Type Culture Collection (ATCC) at 10801 University Boulevard, Manassas, Va. 20110, USA on 8th Apr., 1999 and was assigned ATCC Accession No. 207196.

REFERENCES

1. Altuvia, Y., Schueler, O., and Margalit, H. (1995) *J. Mol. Biol.* 249:244–250.
2. Amann and Brosius (1985). *Gene* 40: 183.
3. Anderson, B. J., M. M. Bills, J. R. Egerton, and J. S. Mattick. (1984) *Journal of Bacteriology* 160:748–754.
4. Ausubel, F. M., Brent, R., Kingston, R E, Moore, D. D., Seidman, J. G., Smith, J. A., and Struhl, K. (1987). In: Current Protocols in Molecular Biology. Wiley Interscience (ISBN 047150338).
5. Barker, I. K. and Van Dreumel, A. A. (1985) In "Pathology of Domestic Animals," 3rd Edition, Vol. 2 p. 1–237, eds K. V. F. Jubb, P. C. Kennedy and N. Palmer. (Academic Press: Orlando).
6. Cole et al. (1985) In: Monoclonal antibodies in cancer therapy, Alan R. Bliss Inc., pp 77–96.
7. Dayhof, M. D. (1978) In: *Nat. Biomed. Res. Found.* Washington D.C. Vol5, Suppl. 3.
8. De Groot, A. S., Carter, E. J., Roberts, C. G. P., Edelson, B. T., Jesdale, B. M., Meister, G. E., Houghten, R. A., Montoya, J., Romulo, R. C., Berzofsky, J. A., and Ramirezm, B. D. L. L. (1995)*Vaccines* 96, Cold Spring Harbor Laboratory, Cold Spring Harbor N.Y.
9. Devereux, J., Haeberli, P. and Smithies, O. (1984). *Nucl. Acids Res.* 12: 387–395.
10. Elwell, M R, Chapman, A L and Frenkel, J K (1981) *Veterinary Pathology* 18: 136–139.
11. Fox, J G, Murphy, J C, Otto, G Pecquet-Goad, ME, Larson, Q H K and Scott J A (1989) *Veterinary Pathology* 26: 515–517.
12. Gabriel, E. Meister, G. E., Caroline, G. P., Roberts, C. G. P., Berzofsky, J. A., and De Groot, A. S. (1995) *Vaccines* 95, Cold Spring Harbor Laboratory, Cold Spring Harbor N.Y.
13. Gebhart, C. J., Ward, G. E., Chang, K. And Kurtz, H. J. (1983). *American Journal of Veterinary Research* 44:361–367.
14. Gish, W and States, D. J. (1993) *Nature Genetics* 3: 266–272.
15. Goodman et al. (1987) *Biopolymers* 26: 525–532.
16. Huse et al. (1989) *Science* 246: 1275–1281.
17. Jones, L. A., Nibbelink, S., and Glock, R. D. (1997) *Am. J. Vet. Res.* 58: 1125–1131.
18. Jonsson, L. and Martinsson, K. (1976) *Acta Veterinaria Scandinavica* 17:223–232.
19. Kohler and Milstein (1975) *Nature* 256: 495–499
20. Kozbor et al. (1983) *Immunol. Today* 4: 72.
21. Lawson, G. H. K., McOrist, S., Jansi, S. and Mackie, R. A. (1993) *Journal of Clinical Microbiology* 31:1136–1142.
22. Love, R. J. and Love, D. M. (1977) *Veterinary Record* 100:473
23. Margalit, H., Spouge, J. L., Cornette, J. L., Cease, K. B., DeLisi, C., and Berzofsky, J. A. (1987) *J. Immunol.* 138:2213–2229.
24. Mason, R W, Monkton, P and Hasse D (1998) *Australian Veterinary Journal* (submitted for publication).
25. McOrist, S., Boid, R., Lawson, G. H. K. and McConnell, I. (1987) *The Veterinary Record* 121:421–422.
26. McOrist, S, Jasni, S, Mackie, R A, Macintyre, N, Neef, N. and Lawson G H K (1993) *Infection and Immunity* 61: 4286–4292.

27. McOrist, S et at (1995) *International Journal of Systematic Bacteriology* 45: 820–825.
28. McPherson, M. J., Quirke, P., and Taylor, G. R. (1991)In: PCR: A Practical Approach. (series editors, D. Rickwood and B. D. Hames) IRL Press Limited, Oxford. pp1–253.
29. Meister, G. E., Roberts, C. G. P., Berzofsky, J. A., and De Groot, A. S. (1995)*Vaccine* 13: 581–591.
30. Mierke et al. (1990) *Int. J. Peptide Protein Research* 35:35–45.
31. Mohapatra, S. S., Cao, Y., Ni, H., and Salo, D. (1995) *Allergy* 50:37–44.
32. Needleman and Wunsch (1970) *J. Mol. Biol.* 48:443–453.
33. O'Neil, I. P. A. (1970) *Veterinary Record* 87:742–747.
34. Parker, K. C., Bednarek, M. A., and Coligan, J. E. (1994) *J. Immunol.* 152:163–175.
35. Portoghese et al. (1990) *J. Med. Chem.* 33:1714–1720.
36. Reinhartz, A., Alajem, S., Samson, A. and Herzberg, M.(1993). *Gene* 136: 221–226.
37. Rowland, A. C. and Lawson, G. H. K. (1976) *Veterinary Record* 97:178–180.
38. Sambrook, J., E. F. Fritsch, and T. Maniatis. (1989) Molecular cloning. A laboratory manual. Second edition. Cold Spring Harbour Laboratory, Cold Spring Harbour, N.Y.
39. Schodeb, T R and Fox J G (1990) *Veterinary Pathology* 27: 73–80.
40. Shimatake and Rosenberg (1981) *Nature* 292: 128.
41. Stills, H. F. (1991). *Infection and immunology* 59: 3227–3236.
42 Straw, B. E. (1990). *Journal of American Veterinary Medical Association* 197: 355–357.
43. Studier and Moffat (1986) *J. Mol. Biol.* 189: 113.
44. Thompson, J. D., Higgins, D. G., and Gibson, T. J. (1994) *Nucl. Acids Res.* 22: 4673–4680.
45. Vajda, S. and DeLisi, C. (1990) Biopolymers 29:1755–1772.
46. van Regenmortel, M. (1992) Molecular dissection of protein antigens. In: Structure of antigens, (van Regenmortel M. ed.) CRC Press, London, pp1–27.

We claim:

1. An isolated or recombinant immunogenic polypeptide comprising a *Lawsonia* spp. OmpH polypeptide set forth in SEQ ID NO: 1.

2. The isolated or recombinant immunogenic polypeptide of claim 1 wherein said polypeptide elicits the production of antibodies against *Lawsonia intracellularis* when administered to an avian or porcine animal.

3. The isolated or recombinant immunogenic polypeptide of claim 2, wherein said polypeptide is encoded by the OmpH-encoding nucleotide sequence of pALK13 (ATCC 207196).

4. The isolated or recombinant immunogenic polypeptide of claim 3 consisting essentially of the amino acid sequence of SEQ ID NO: 1 or the amino acid sequence encoded by the OmpH-encoding nucleotide sequence of ALK13 (ATCC 207196).

* * * * *

SEQUENCE LISTING

<160> NUMBER OF SEQ ID NOS: 13

<210> SEQ ID NO 1
<211> LENGTH: 186
<212> TYPE: PRT
<213> ORGANISM: Lawsonia intracellularis

<400> SEQUENCE: 1

Met Lys Val Lys Thr Leu Ser Met Ala Ile Leu Ala Cys Leu Leu Val
1               5                   10                  15

Ala Asn Ser Ala Phe Ser Ala Asp Phe Pro Ile Gly Val Phe Asn Ser
            20                  25                  30

Gln Ser Ile Ala Met Glu Ser Glu Ala Ala Lys Ala Ala Gln Lys Lys
        35                  40                  45

Leu Gln Ser Glu Phe Gly Asn Glu Lys Thr Gln Leu Glu Lys Gln Ala
    50                  55                  60

Lys Asp Leu Gln Thr Lys Ala Asp Asp Leu Gln Ala Lys Ser Ala Ala
65                  70                  75                  80

Met Ser Asn Gln Ala Arg Glu Asp Lys Gln Arg Glu Phe Leu Glu Leu
                85                  90                  95

Arg Arg Asn Phe Glu Glu Lys Ser Arg Asp Phe Ala Ile Arg Val Glu
            100                 105                 110

Gln Ala Glu Asn Thr Leu Arg Gln Tyr Leu Ala Glu Gln Ile Tyr Leu
        115                 120                 125

Ala Ala Glu Thr Ile Ala Lys Lys Lys Gly Leu Lys Leu Val Leu Asp
    130                 135                 140

Ser Ala Ser Gly Ser Val Met Tyr Leu Glu Lys Asn Leu Asp Ile Thr
145                 150                 155                 160

Lys Glu Ile Leu Glu Ala Ile Asn Ala Ala Trp Lys Lys Gly Gly Ser
                165                 170                 175

Lys Leu Pro Glu Met Ala Asn Arg Lys Lys
            180                 185

<210> SEQ ID NO 2
<211> LENGTH: 561
<212> TYPE: DNA
<213> ORGANISM: Lawsonia intracellularis

```
<220> FEATURE:
<221> NAME/KEY: CDS
<222> LOCATION: (1)...(561)

<400> SEQUENCE: 2 atg aaa gta aaa act ctt tcc atg gct att tta gct tgt tta tta gta      48
Met Lys Val Lys Thr Leu Ser Met Ala Ile Leu Ala Cys Leu Leu Val
 1               5                  10                  15 gct aac agt gca ttt tcg gct gac ttc cct att ggt gtc ttt aat tct      96
Ala Asn Ser Ala Phe Ser Ala Asp Phe Pro Ile Gly Val Phe Asn Ser
             20                  25                  30 caa tcc att gcc atg gag agt gaa gca gct aag gcc gct caa aaa aaa    144
Gln Ser Ile Ala Met Glu Ser Glu Ala Ala Lys Ala Ala Gln Lys Lys
         35                  40                  45 tta caa tca gaa ttt ggt aat gaa aaa aca caa ctt gaa aaa caa gca    192
Leu Gln Ser Glu Phe Gly Asn Glu Lys Thr Gln Leu Glu Lys Gln Ala
 50                  55                  60 aaa gat ttg caa aca aaa gct gat gat tta caa gct aag tca gca gct    240
Lys Asp Leu Gln Thr Lys Ala Asp Asp Leu Gln Ala Lys Ser Ala Ala
 65                  70                  75                  80 atg tct aac caa gca cgt gaa gat aaa caa aga gaa ttt ctt gaa ctt    288
Met Ser Asn Gln Ala Arg Glu Asp Lys Gln Arg Glu Phe Leu Glu Leu
                 85                  90                  95 cgt cgt aat ttc gaa gaa aaa tct cgt gac ttt gca ata cgt gtc gaa    336
Arg Arg Asn Phe Glu Glu Lys Ser Arg Asp Phe Ala Ile Arg Val Glu
            100                 105                 110 caa gct gaa aac aca tta cgt caa tat cta gct gaa caa atc tat ctt    384
Gln Ala Glu Asn Thr Leu Arg Gln Tyr Leu Ala Glu Gln Ile Tyr Leu
        115                 120                 125 gct gct gaa act ata gca aaa aag aaa ggg tta aaa ctt gtt ctt gat    432
Ala Ala Glu Thr Ile Ala Lys Lys Lys Gly Leu Lys Leu Val Leu Asp
    130                 135                 140 agt gct agt gga agt gta atg tac ctt gaa aaa aat cta gat att aca    480
Ser Ala Ser Gly Ser Val Met Tyr Leu Glu Lys Asn Leu Asp Ile Thr
145                 150                 155                 160 aaa gaa att ctt gaa gcc ata aat gct gca tgg aaa aaa ggt gga agt    528
Lys Glu Ile Leu Glu Ala Ile Asn Ala Ala Trp Lys Lys Gly Gly Ser
                165                 170                 175 aaa ctt cca gag atg gca aac cgg aaa aaa taa                        561
Lys Leu Pro Glu Met Ala Asn Arg Lys Lys  *
            180                 185

<210> SEQ ID NO 3
<211> LENGTH: 23
<212> TYPE: DNA
<213> ORGANISM: Artificial Sequence
<220> FEATURE:
<223> OTHER INFORMATION: oligonucleotide primer RA176 forward

<400> SEQUENCE: 3
tttattcatt cagaaggagc ttc                                           23

<210> SEQ ID NO 4
<211> LENGTH: 21
<212> TYPE: DNA
<213> ORGANISM: Artificial Sequence
<220> FEATURE:
<223> OTHER INFORMATION: oligonucleotide primer RA177 reverse

<400> SEQUENCE: 4
aagtttagca atttctgaaa g                                             21
```

-continued

<210> SEQ ID NO 5
<211> LENGTH: 143
<212> TYPE: PRT
<213> ORGANISM: Yersinia pseudotuberculosis

<400> SEQUENCE: 5

Ser Ser Ile Phe Gln Gln Leu Pro Ala Arg Glu Ala Val Ala Ala Gly
1               5                   10                  15

Lys Lys Gln Leu Glu Asn Glu Phe Lys Gly Arg Ala Thr Glu Leu Gln
20 25 30

Gly Ile Ala Ile Val Asn Val Met Glu Arg Asp Leu Gln Thr Lys Met
35 40 45

Gln Lys Leu Gln Arg Asp Gly Ser Thr Met Lys Ala Ser Asp Arg Thr
50 55 60

Lys Ile Leu Ser Arg Ile Gln Asp Ala Val Lys Ser Val Ala Thr Leu
65 70 75 80

Glu Asn Glu Val Met Lys Gln Arg Glu Thr Lys Gly Gly Tyr Asp Val
85 90 95

Val Ile Asp Ala Asn Ala Val Ala Tyr Ala Asp Ser Ser Phe Ser Thr
100 105 110

Lys Ala Gln Ala Phe Glu Gln Asp Asn Arg Arg Arg Gln Ala Glu Glu
115 120 125

Arg Asn Lys Lys Asp Ile Thr Ala Asp Val Leu Lys Gln Val Lys
130 135 140

<210> SEQ ID NO 6
<211> LENGTH: 164
<212> TYPE: PRT
<213> ORGANISM: Yersinia enterocolitica

<400> SEQUENCE: 6

Met Lys Lys Ser Ser Ile Phe Gln Gln Leu Pro Ala Arg Glu Thr Val
1 5 10 15

Ala Trp Leu Cys Ala Ala Ser Leu Gly Leu Ala Leu Ala Ala Ser Ala
20 25 30

Arg Val Gln Ala Ala Lys Ile Lys Gln Leu Glu Asn Glu Phe Lys Gly
35 40 45

Arg Ala Thr Glu Leu Gln Gly Ala Ile Val Asn Val Met Glu Arg Asp
50 55 60

Leu Gln Thr Lys Met Gln Lys Leu Gln Arg Asp Gly Ser Thr Met Lys
65 70 75 80

Ala Ser Asp Arg Thr Lys Ile Leu Ser Arg Ile Gln Asp Ala Val Lys
85 90 95

Ser Val Ala Ser Leu Glu Asn Asp Val Met Lys Gln Arg Glu Thr Lys
100 105 110

Gly Gly Tyr Asp Val Val Ile Asp Ala Asn Ala Val Ala Tyr Ala Asp
115 120 125

Pro Ser Phe Ser Thr Lys Ala Gln Ala Phe Glu Gln Asp Asn Arg Arg
130 135 140

Arg Gln Met Glu Glu Arg Asn Lys Lys Asp Ile Thr Ala Asp Val Leu
145 150 155 160

Lys Gln Val Lys

<210> SEQ ID NO 7
<211> LENGTH: 197
<212> TYPE: PRT
<213> ORGANISM: Haemophilus influenzae

```
<400> SEQUENCE: 7

Met Lys Asn Ile Gly Tyr Ile Phe Gln His His Pro Asp Arg Gln Ala
1               5                  10                  15

Val Ala Ala Lys Val Thr Ala Leu Ala Leu Gly Ile Ala Leu Ala Ser
            20                  25                  30

Gly Tyr Ala Ser Ala Glu Glu Lys Asp Lys Leu Asp Ala Glu Phe Lys
                35                  40                  45

Pro Val Ala Glu Lys Leu Ala Ala Ser Lys Ile Ala Phe Ile Asn Ala
    50                  55                  60

Lys Glu Val Asp Asp Lys Ile Ala Ala Arg Lys Lys Val Glu Ala
65                  70                  75                  80

Lys Val Ala Ala Leu Glu Lys Asp Ala Pro Arg Leu Arg Gln Ala Asp
                85                  90                  95

Ile Gln Lys Leu Leu Asp Ser Ile Gln Thr Ala Thr Asn Asn Leu Ala
                100                 105                 110

Lys Arg Gln Gln Glu Ile Asn Lys Leu Gly Ala Ala Glu Asp Ala Glu
            115                 120                 125

Leu Gln Lys Leu Met Gln Glu Ala Lys Gly Tyr Thr Tyr Val Leu Asp
    130                 135                 140

Ala Asn Ser Ile Val Phe Ala Val Glu Gly Leu Arg Lys Leu Gln Val
145                 150                 155                 160

Glu Ala Gln Ser Lys Leu Ser Arg Lys Lys Ala Glu Leu Glu Lys Met
                165                 170                 175

Lys Asp Ile Thr Glu Glu Val Leu Lys Ser Ile Pro Ala Ser Glu Lys
            180                 185                 190

Ala Gln Glu Lys Lys
        195

<210> SEQ ID NO 8
<211> LENGTH: 162
<212> TYPE: PRT
<213> ORGANISM: Aquifex aeolicus

<400> SEQUENCE: 8

Met Glu Gly Asn Lys Val Ile Arg Glu Ser Lys Phe Ile Ala Lys Ala
1               5                   10                  15

Gln Ile Met Lys Lys Phe Phe Ala Leu Met Thr Leu Ile Ala Gly Ile
            20                  25                  30

Ser Phe Ser Leu Asp Thr Glu Leu Arg Lys Glu Leu Glu Lys Tyr Gln
                35                  40                  45

Lys Leu Ile Gln Glu Phe Ala Cys Val Asp Thr Lys Gln Lys Lys Leu
    50                  55                  60

Glu Ala Leu Lys Lys Ser Leu Glu Ser Lys Ala Leu Ser Glu Lys Ala
65                  70                  75                  80

Lys Glu Lys Val Phe Asp Lys Val Ile Lys Ile Val Glu Ser Thr Ala
                85                  90                  95

Lys Lys Ala Lys Glu Ile Glu Gln Leu Glu Asp Glu Lys Lys Lys Ile
            100                 105                 110

Lys Ala Val Phe Asp Cys Asn Ser Met Leu Tyr Trp Asp Lys Lys Leu
            115                 120                 125

Arg Lys Leu Gln Val Glu Ala Gln Ser Lys Leu Ser Arg Lys Lys Ala
    130                 135                 140
```

```
Glu Leu Glu Lys Met Ile Asp Ile Thr Asn Glu Val Leu Lys Glu Leu
145                 150                 155                 160

Asp Lys

<210> SEQ ID NO 9
<211> LENGTH: 161
<212> TYPE: PRT
<213> ORGANISM: Escherichia coli

<400> SEQUENCE: 9

Met Lys Lys Gly Ser Leu Phe Gln Gln Val Ala Gln Lys Thr Gly Val
1               5                   10                  15

Ser Trp Leu Leu Ala Ala Gly Leu Gly Leu Ala Leu Ala Thr Ser Ala
                20                  25                  30

Gln Ala Ala Asp Lys Ile Asn Thr Leu Glu Asn Glu Phe Lys Gly Arg
            35                  40                  45

Ala Ser Glu Leu Gln Arg Ala Ile Val Asn Met Met Glu Thr Asp Leu
    50                  55                  60

Gln Ala Lys Met Lys Lys Leu Gln Ser Met Lys Ala Gly Ser Asp Arg
65                  70                  75                  80

Thr Lys Leu Val Thr Arg Ile Gln Thr Ala Val Lys Ser Val Ala Asn
                85                  90                  95

Leu Glu Lys Asp Val Met Ala Gln Arg Gln Thr Ser Gln Asp Ile Asp
            100                 105                 110

Leu Val Val Asp Ala Asn Ala Val Ala Tyr Asn Ser Ser Asp Val Phe
        115                 120                 125

Ala Gln Lys Ala Gln Ala Phe Glu Gln Asp Arg Ala Arg Arg Ser Asn
    130                 135                 140

Glu Glu Arg Gly Lys Lys Asp Ile Thr Ala Asp Val Leu Lys Gln Val
145                 150                 155                 160

Lys

<210> SEQ ID NO 10
<211> LENGTH: 161
<212> TYPE: PRT
<213> ORGANISM: Streptococcus typhi

<400> SEQUENCE: 10

Met Lys Lys Gly Asn Leu Phe Gln Gln Val Ala Gln Lys Thr Gly Val
1               5                   10                  15

Ser Trp Leu Leu Ala Ala Gly Leu Gly Leu Ala Met Val Thr Ser Ala
                20                  25                  30

Gln Ala Ala Asp Lys Ile Asn Thr Leu Glu Asn Glu Phe Lys Gly Arg
            35                  40                  45

Ala Ala Glu Leu Gln Lys Ala Ile Val Asn Met Met Glu Thr Asp Leu
    50                  55                  60

Gln Ser Lys Met Gln Arg Leu Gln Ser Met Lys Ala Gly Ser Asp Arg
65                  70                  75                  80

Thr Lys Leu Val Thr Arg Ile Gln Thr Ala Val Lys Lys Val Ala Asn
                85                  90                  95

Leu Glu Lys Asp Val Met Ser Gln Arg Gln Thr Asp Gln Ser Ile Asp
            100                 105                 110

Leu Val Val Asp Ala Asn Thr Val Ala Tyr Asn Ser Ser Asp Val Phe
        115                 120                 125

Ala Gln Lys Ala Gln Ala Phe Glu Lys Asp Arg Ala Arg Arg Ser Asn
    130                 135                 140
```

```
Glu Glu Arg Asn Lys Lys Asp Ile Thr Ala Asp Val Leu Lys Gln Val
145                 150                 155                 160

Lys
```

<210> SEQ ID NO 11
<211> LENGTH: 177
<212> TYPE: PRT
<213> ORGANISM: Chlamidia trachomatis

<400> SEQUENCE: 11

```
Met Lys Lys Phe Arg Arg Cys Leu Glu Glu Ser Ala Leu Gly Lys Lys
1               5                   10                  15

Glu Ser Leu Leu Leu Ser Leu Met Ser Leu Ser Ser Leu Pro Thr Phe
                20                  25                  30

Ala Ala Asn Ser Thr Gly Thr Ala Glu Phe Glu Lys Met Lys Asn Gln
            35                  40                  45

Phe Ser Asn Ser Met Gly Lys Ile Gly Ile Val Asn Leu Met Glu Glu
        50                  55                  60

Glu Leu Ser Ser Ile Tyr Ser Lys Leu Gln Asp Asp Tyr Met Glu
65                  70                  75                  80

Gly Leu Ser Glu Thr Ala Ala Glu Ile Met Glu Glu Val Lys Lys
                85                  90                  95

Ala Ser Glu Thr Val Arg Ile Leu Arg Lys Lys Phe Glu Asp Leu Ser
            100                 105                 110

Ala Glu Gln Glu Gly Leu Ser Val Leu Leu Asn Glu Asp Ile Val Leu
        115                 120                 125

Ser Ile Asp Ser Ser Tyr Asn Thr Ala Gln Gly Gln Tyr Tyr Gln Ile
    130                 135                 140

Leu Asn Gln Ser Asn Leu Lys Arg Met Gln Lys Ala Asp Lys Thr Asp
145                 150                 155                 160

Ala Val Ile Lys Val Leu Asp Val Leu Phe Lys Ile Ile Asn Met Arg
                165                 170                 175

Ser
```

<210> SEQ ID NO 12
<211> LENGTH: 227
<212> TYPE: PRT
<213> ORGANISM: Streptococcus pyogenes

<400> SEQUENCE: 12

```
Met Ala Lys Asn Asn Thr Asn Arg His Tyr Ser Leu Arg Lys Leu Lys
1               5                   10                  15

Ile Gln Asn Ile Arg Leu Arg His Glu Asn Lys Asp Leu Lys Ala Arg
                20                  25                  30

Thr Gly Thr Ala Ser Val Ala Val Ala Leu Thr Val Leu Gly Ala Gly
            35                  40                  45

Phe Ala Asn Gln Thr Glu Leu Glu Asn Ala Met Glu Val Ala Gly Arg
        50                  55                  60

Asp Phe Lys Arg Ala Glu Glu Leu Glu Lys Ala Lys Val Lys Ala Asn
65                  70                  75                  80

Gly Asp Gly Asn Pro Arg Glu Val Ile Glu Asp Leu Ala Ala Asn Asn
                85                  90                  95

Pro Ala Gln Ala Leu Glu Asp Gln Arg Lys Asp Leu Glu Thr Lys Leu
            100                 105                 110
```

```
Lys Glu Leu Gln Gln Asp Tyr Asp Leu Ala Lys Glu Ser Thr Ser Trp
        115                 120                 125

Asp Arg Gln Arg Glu Glu Lys Lys Ala Leu Glu Leu Ala Ile Asp
130                 135                 140

Gln Ala Ser Gln Leu Glu Lys Glu Leu Glu Lys Lys Glu Ala Asp
145                 150                 155                 160

Tyr Asn Arg Ala Asn Val Leu Glu Lys Glu Leu Glu Thr Ile Thr Arg
                165                 170                 175

Glu Gln Glu Ile Asn Leu Glu Leu Ala Ile Asp Gln Ala Ser Arg Asp
                180                 185                 190

Tyr His Arg Ala Thr Ala Leu Glu Lys Glu Leu Arg Asn Leu Leu Gly
                195                 200                 205

Asn Ala Lys Leu Glu Leu Asp Gln Leu Ser Ser Glu Lys Glu Gln Leu
210                 215                 220

Thr Ile Arg
225

<210> SEQ ID NO 13
<211> LENGTH: 199
<212> TYPE: PRT
<213> ORGANISM: Unknown
<220> FEATURE:
<223> OTHER INFORMATION: Sequence 1 from WO 97/01638
<220> FEATURE:
<221> NAME/KEY: VARIANT
<222> LOCATION: (1)...(199)
<223> OTHER INFORMATION: Xaa = Any Amino Acid

<400> SEQUENCE: 13

Met Lys Asn Ile Gly Tyr Ile Phe His His Pro Asp Arg Gln Ala Val
1               5                   10                  15

Ala Ala Lys Val Thr Ala Leu Ala Leu Gly Ile Ala Leu Ala Ser Gly
                20                  25                  30

Tyr Ala Ser Ala Glu Glu Lys Asp Lys Leu Asp Ala Glu Phe Lys Pro
            35                  40                  45

Val Ala Glu Lys Leu Ala Ala Ser Lys Ile Ala Phe Ile Asn Ala Lys
50                  55                  60

Glu Val Asp Asp Lys Ile Ala Ala Arg Lys Lys Val Glu Ala Lys
65                  70                  75                  80

Val Ala Ala Leu Glu Lys Asp Ala Pro Arg Leu Arg Gln Ala Asp Ile
                85                  90                  95

Gln Lys Leu Leu Asp Ser Ile Gln Thr Ala Thr Asn Asn Leu Ala Arg
                100                 105                 110

Arg Gln Glu Glu Ile Asn Lys Leu Gly Ala Ala Glu Asp Ala Glu Leu
            115                 120                 125

Gln Lys Leu Met Gln Glu Ala Lys Gly Tyr Thr Tyr Val Leu Asp Ala
            130                 135                 140

Asn Ser Val Val Phe Ala Val Glu Gly Gln Asp Lys Lys Val Gln Glu
145                 150                 155                 160

Phe Gln Ala Gln Asn Glu Lys Arg Gln Ala Glu Glu Arg Gly Lys Lys
                165                 170                 175

Asp Ile Thr Glu Glu Val Leu Lys Ser Ile Pro Ala Ser Glu Lys Ala
            180                 185                 190

Gln Phe Lys Lys Xaa Xaa Val
            195
```